(12) United States Patent
Ikemizu et al.

(10) Patent No.: US 7,624,601 B2
(45) Date of Patent: Dec. 1, 2009

(54) WATER SUPPLY DEVICE, WATER SUPPLY METHOD, AND WASHING MACHINE HAVING WATER SUPPLY DEVICE

(75) Inventors: Mugihei Ikemizu, Osaka (JP); Hirofumi Yoshikawa, Osaka (JP); Rie Hiramoto, Yamatokoriyama (JP); Minoru Tadano, Sakai (JP); Hirokazu Ohe, Yao (JP)

(73) Assignee: Sharp Kabushiki Kaisha, Osaka (JP)

( * ) Notice: Subject to any disclaimer, the term of this patent is extended or adjusted under 35 U.S.C. 154(b) by 572 days.

(21) Appl. No.: 10/564,692

(22) PCT Filed: Jun. 15, 2004

(86) PCT No.: PCT/JP2004/008336

§ 371 (c)(1),
(2), (4) Date: Jan. 13, 2006

(87) PCT Pub. No.: WO2005/014911

PCT Pub. Date: Feb. 17, 2005

(65) Prior Publication Data

US 2006/0186222 A1 Aug. 24, 2006

(30) Foreign Application Priority Data

Aug. 8, 2003 (JP) .............................. 2003-206684
Nov. 7, 2003 (JP) .............................. 2003-378009

(51) Int. Cl.
*D06F 39/02* (2006.01)
(52) U.S. Cl. ...................................... 68/17 R; 68/13 A
(58) Field of Classification Search .................. 68/3 R, 68/17 R, 13 A
See application file for complete search history.

(56) References Cited

U.S. PATENT DOCUMENTS 1,157,233 A * 10/1915 Lashmet ...................... 204/212

(Continued)

FOREIGN PATENT DOCUMENTS

JP 58-041599 3/1983

(Continued)

OTHER PUBLICATIONS

International Search Report for corresponding PCT/JP2004/008336, mailed Sep. 28, 2004.

(Continued)

*Primary Examiner*—Frankie L Stinson
(74) *Attorney, Agent, or Firm*—Renner, Otto, Boisselle & Sklar, LLP

(57) ABSTRACT

A water feeding apparatus (300) has an ion eluter (100) and a shower emitter (200). The shower emitter (200) receives water via a coupling pipe (250) from the ion eluter (100), and sprays the water, in the form of a shower, onto laundry. Liquid droplets in the form of a shower are small and easy to dry, and thus produce crystals having smaller particles (with large surface areas), having more lattice defects, and easier to dissolve. With these crystals attached to the laundry, when the crystals make contact with moisture next time, the silver ion in the liquid droplets easily dissolves. Even when the laundry is made of water-repellent or hydrophobic cloth, the solution dries up on the surface of the cloth before water is repelled. Thus, even this type of laundry can benefit from the antimicrobial effect of the silver ion.

27 Claims, 16 Drawing Sheets

U.S. PATENT DOCUMENTS

| | | | | |
|---|---|---|---|---|
| 1,219,333 | A | * | 3/1917 | Kynaston .................... 204/240 |
| 3,386,582 | A | | 6/1968 | Brezosky et al. |
| 3,432,420 | A | * | 3/1969 | Pei-Tai ........................ 204/216 |
| 3,680,703 | A | * | 8/1972 | Borochaner ................. 210/136 |
| 3,869,382 | A | * | 3/1975 | Tejeda ......................... 210/662 |
| 3,936,364 | A | * | 2/1976 | Middle ......................... 426/66 |
| 4,451,341 | A | * | 5/1984 | Miller .......................... 205/743 |
| 4,525,253 | A | * | 6/1985 | Hayes et al. ................ 210/748 |
| 5,029,458 | A | * | 7/1991 | Obata et al. .................. 68/19.2 |
| 5,091,152 | A | * | 2/1992 | Thomas, Sr. .............. 204/228.6 |
| 5,345,637 | A | * | 9/1994 | Pastryk et al. .................. 8/158 |
| 5,876,575 | A | * | 3/1999 | Kump ........................... 204/248 |
| 5,958,213 | A | * | 9/1999 | Goto .......................... 205/754 |
| 6,350,385 | B1 | * | 2/2002 | Holt et al. .................... 210/748 |
| 6,743,351 | B1 | * | 6/2004 | Arai et al. .................... 205/701 |
| 6,852,236 | B2 | * | 2/2005 | Holt et al. .................... 210/748 |
| 6,954,995 | B2 | * | 10/2005 | Kitamura et al. .............. 34/597 |
| 7,296,444 | B2 | * | 11/2007 | Mae et al. .................. 68/12.04 |
| 7,322,065 | B2 | * | 1/2008 | Kim et al. ....................... 8/158 |
| 2004/0205899 | A1 | * | 10/2004 | Park et al. ...................... 8/159 |

FOREIGN PATENT DOCUMENTS

| | | | |
|---|---|---|---|
| JP | 58-124493 | | 7/1983 |
| JP | 58-133300 | | 8/1983 |
| JP | 60-176692 | | 9/1985 |
| JP | 63-051991 | * | 3/1988 |
| JP | 1-148300 | | 6/1989 |
| JP | 1-167392 | | 11/1989 |
| JP | 05-111595 | * | 5/1993 |
| JP | 5-74487 | | 10/1993 |
| JP | 06-343791 | | 12/1994 |
| JP | 07-008696 | | 1/1995 |
| JP | 07-047197 | | 2/1995 |
| JP | 07-163783 | | 6/1995 |
| JP | 08-150289 | | 6/1996 |
| JP | 8-192161 | | 7/1996 |
| JP | 08-206399 | | 8/1996 |
| JP | 09-108490 | | 4/1997 |
| JP | 10-043462 | | 2/1998 |
| JP | 10-179699 | * | 7/1998 |
| JP | 11-028473 | * | 2/1999 |
| JP | 11-137888 | | 5/1999 |
| JP | 11-207352 | | 8/1999 |
| JP | 2000-176461 | * | 6/2000 |
| JP | 2000-308793 | | 11/2000 |
| JP | 2000-325959 | * | 11/2000 |
| JP | 2001-029306 | | 2/2001 |
| JP | 2001-029688 | | 2/2001 |
| JP | 2001-046794 | | 2/2001 |
| JP | 2001-113288 | | 4/2001 |
| JP | 2001-120888 | | 5/2001 |
| JP | 2001-276472 | | 10/2001 |
| JP | 2001-276484 | | 10/2001 |
| JP | 2002-113288 | * | 4/2002 |
| JP | 2003-305472 | * | 10/2003 |
| JP | 2004-024597 | | 1/2004 |
| JP | 2004-057423 | | 2/2004 |
| JP | 2004-166938 | | 6/2004 |
| KR | 1020020012368 | | 2/2002 |
| KR | 1020020012369 | | 2/2002 |
| KR | 1020020075483 | | 10/2002 |

OTHER PUBLICATIONS

Sharp Kabushiki Kaisha, "Winter Full-line Catalog of washing Machines", p. 1-3 2002 (English translation of relevant portions being submitted).

* cited by examiner

FIG.11

| No. | COURSE | PROCESS TYPE | | | |
|---|---|---|---|---|---|
| | | WASHING | RINSING | SPIN-DRYING | DRYING |
| (1) | STANDARD | ○ | ○ | ○ | ○ |
| (2) | SILVER ION SHOWER (RINSING1) | ○ | IN SHOWER RINSING ◎ | ○ | ○ |
| (3) | SILVER ION SHOWER (RINSING2) | ○ | IN STORED-WATER RINSING ◎ | ○ | ○ |
| (4) | SILVER ION SHOWER (SPIN-DRYING) | ○ | ○ | ◎ | ○ |
| (5) | SILVER ION SHOWER (RINSING&SPIN-DRYING) | ○ | IN STORED-WATER RINSING ◎ | ◎ | ○ |
| (6) | SILVER ION SHOWER (DRYING) | ○ | ○ | ○ | ◎ |

○: PROCESS TYPE PERFORMED
◎: SHOWER EMITTED DURING PROCESS

WATER SUPPLY DEVICE, WATER SUPPLY METHOD, AND WASHING MACHINE HAVING WATER SUPPLY DEVICE

TECHNICAL FIELD

The present invention relates to an apparatus and a method for feeding water which, when water is fed to a target (for example, laundry) to be fed with water, permit a substance (for example, the silver ion, a softening agent, or a sustained-release agent), dissolved in the water to exert the effect thereof more easily. The present invention also relates to a washer incorporating such an apparatus for feeding water.

BACKGROUND ART

When laundry is washed in a washer, it is common to add a treatment substance to the water (in particular the water for rinsing) used. Common examples of such treatment substances are softening agents and starching agents. In addition to these, there has recently been a growing demand for treatment for making laundry antimicrobial.

From a hygienic perspective, it is desirable to hang and dry laundry in the sun. In recent years, however, as more women go to work and more families become nuclear, there have been an increasing number of households where no one is present in the house during the daytime. In such a household, there is no choice but to hang and dry laundry indoors. Even in a household where someone is present during the daytime, when it rains, it is necessary to hang and dry laundry indoors.

When laundry is hung and dried indoors, it is more prone to proliferation of bacteria and mold than when hung and dried in the sun. This tendency is remarkable when it takes a comparatively long time to dry laundry because of high humidity combined with low temperature as in a rainy season. Depending on the degree of microbial proliferation, laundry may come to give off foul odors.

In recent years, as people become increasingly economy-conscious, there has been an increase in the number of households that reuse bath water after bathing. However, bath water, when stored overnight, contains bacteria that has proliferated therein, and these bacteria stick to laundry and further proliferate therein, causing foul odors.

For this reason, in households where laundry is routinely hung and dried indoors and where bath water is often reused for washing, there is a strong demand for treatment for making textile fabrics antimicrobial.

On the other hand, nowadays, many clothes are available that are made of fibers previously treated with antimicrobial and deodorizing treatment or microbe-controlling treatment. However, it is difficult to replace all the textile fabrics used in a household with those previously treated with antimicrobial and deodorizing treatment. Moreover, as those textile fabrics are washed repeatedly, the effect of antimicrobial and deodorizing treatment gradually diminishes.

Here comes the idea of treating laundry with antimicrobial treatment every time it is washed. For example, Patent Publications 1 and 2 listed below disclose washers wherein a voltage is applied between silver electrodes so that the silver ion is added to washing water. Patent Publication 3 listed below discloses a washer provided with a silver elution cartridge that elutes silver by making a silver elution material (for example, silver sulfide) react with hypochlorous acid present in tap water. These washers achieve antimicrobial treatment of laundry by dipping laundry in water containing an antimicrobial metallic ion to make the metallic ion attach to the laundry.

Patent Publication 1:
  Japanese Utility Model Application Laid-Open No. H5-74487 (laid-open on Oct. 12, 1993)
Patent Publication 2:
  Japanese Patent Application Laid-Open No. 2001-276484 (laid-open on Oct. 9, 2001)
Patent Publication 3:
  Japanese Patent Application Laid-Open No. 2002-113288 (laid-open on Apr. 16, 2002)

Apart from the antimicrobial treatment described above, in recent years, there have been proposed various washers wherein water is fed in in the form of a mist during a spin-drying stage involved in a rinsing process performed in a washing procedure (for example, see Patent Publications 4, 5, and 6 listed below). In these washers, water in the form of a mist is fed into a tub shared for washing and spin-drying. This achieves the effects of, to name a few, preventing the splashing of water inside the tub, permitting laundry, which contain air, to become familiar with water, and washing soil off the interior of the tub.

Patent Publication 4:
  Japanese Patent Application Laid-Open Nos. 2001-29688 (laid-open on Feb. 6, 2001)
Patent Publication 5:
  Japanese Patent Application Laid-Open No. 2001-276472 (laid-open on Oct. 9, 2001)
Patent Publication 6:
  Japanese Patent Application Laid-Open No. 2003-10584 (laid-open on Jan. 14, 2003)

DISCLOSURE OF THE INVENTION

Problems to be Solved by the Invention

As laundry once dipped in metallic ion water (for example, silver ion water) dries up, the silver ion water that has penetrated the laundry dries out. When this happens, the silver ion contained in the silver ion water precipitates in the form of a fine crystalline powder of metallic silver and silver compounds such as silver oxide, and remains on the surface of the laundry. When these silver compounds make contact with water next time, the silver ion is eluted from the surface of the silver compounds, and the silver ion starts to exert an antimicrobial effect.

Here, the antimicrobial effect of the silver ion can be obtained more effectively by making it easier for the silver ion to be eluted from the silver compounds remaining on the surface of laundry. One way to achieve this is to quicken the drying of silver ion water. By quickening the drying of silver ion water, it is possible to quicken the precipitation of crystals of the silver compounds, and as a result it is possible to obtain crystals with finer particles and with more lattice defects. Since the dissolution of crystals occurs at lattice defects including the surfaces of the crystals, the smaller the particles of crystals (i.e., the larger the surface areas thereof), and the more lattice defects the crystals have, the more easily the crystals dissolve.

However, in constructions, like those disclosed in Patent Publications 1 to 3, where laundry is dipped in silver ion water, the liquid droplets of silver ion water that attach to the surface of the laundry is large, and thus it takes a considerable time for the silver ion water to dry out. This results in silver compounds forming crystals with larger particles and with fewer lattice defects. Thus, when the silver compounds make contact with water next time, it is difficult for the silver ion to be eluted, and this makes it impossible to effectively obtain the antimicrobial effect of the silver ion.

Incidentally, the drying of silver ion water can be quickened by drying laundry with the target drying temperature raised, i.e., by blowing warmer air onto the laundry. This, however, is undesirable because of the risk of damaging laundry.

Moreover, with a method whereby laundry is dipped in silver ion water, articles of laundry that are made of water-repellent cloth repel silver ion water, and therefore almost no part of the silver ion water remains on the surface of such articles. Even articles of laundry that are made of not so far as water-repellent but hydrophobic cloth such as chemical fiber suck little water, and accordingly, even when such articles are dipped in silver ion water, the silver ion water does not penetrate them. As a result, with either of these types of laundry, it is impossible to effectively make silver compounds attach to the surface of the laundry, and thus it is impossible to surely obtain the antimicrobial effect of the silver ion eluted from the silver compounds.

The descriptions above deal only with washers that use silver ion water to discuss problems experienced therewith. Such problems are experienced, however, not only with washers but water feeding apparatuses in general that exploit the effect peculiar to a substance that is initially dissolved in water, but then crystallizes as the water dries up, and then exerts the effect thereof when dissolved in water again.

The present invention is devised to solve the problems mentioned above. Accordingly, it is an object of the present invention to provide an apparatus and a method for feeding water and a washer incorporating such an apparatus which permit easier exertion of the effect peculiar to a substance that is initially dissolved in water, but then crystallizes as the water dries up, and then exerts the effect thereof when dissolved in water again, and which permit this effect to be obtained surely.

Means for Solving the Problem (1) According to the present invention, a water feeding apparatus for feeding water to a target to be fed with water is provided with: an adder for adding a treatment substance to the water; and a shower emitter for spraying, in the form of a shower, the water fed thereto via the adder onto the target.

Liquid droplets in the form of a shower have a larger surface area than the same amount of water, and thus make contact with air over a larger area. Accordingly, when shower water is sprayed onto the target, the water attached to the target dries more easily.

As a result, the treatment substance dissolved in the water precipitates more quickly, making it possible to form crystals with smaller particles (i.e., with larger surface areas) and with more lattice defects). Since the dissolution of crystals occurs at lattice defects including the surfaces of the crystals, the smaller the particles of crystals (i.e., the larger the surface areas thereof), and the more lattice defects the crystals have, the more easily the crystals dissolve.

According to the present invention, small water particles (liquid droplets) that permit the treatment substance to be easily eluted as a result of the dissolution of crystals are generated and sprayed onto the target by the shower emitter. This makes it easy for the treatment substance to exert the effect thereof (for example, an antimicrobial effect). Thus, it is possible to surely obtain the effect peculiar to the treatment substance.

Moreover, even when the target is water-repellant or hydrophobic cloth, by spraying shower water onto the cloth, it is possible to surely make the treatment substance contained in the shower water attach to the surface of the cloth. That is, the liquid droplets of the shower water are small, and are thus easy to dry. Accordingly, they dry up before being repelled on the surface of the cloth, permitting the treatment substance contained in the shower water to attach to the surface of the cloth. Thus, even with a target, such as water-repellant or hydrophobic cloth, that the treatment substance is difficult to penetrate, it is possible to surely obtain the effect (for example, an antimicrobial effect) that the treatment substance exerts when eluted.

Incidentally, the washers disclosed in Patent Publications 4 to 6 feed only water in the form of a mist to the target, and do not involve a construction "provided with an adder for adding a treatment substance to water wherein the water obtained via the adder is sprayed in the form of a shower onto the target". Thus, none of these related-art publications discloses at least the idea of spraying, in the form of a shower, water mixed with a treatment substance. That is, in this respect, the present invention is markedly different from what is disclosed in these related-art publications.

(2) In the water feeding apparatus of the invention, the adder may be an ion eluter that elutes an ion as the treatment substance and that adds the ion to the water passing therethrough.

By using an ion eluter as the adder, it is possible to spray water containing an ion serving as the treatment substance from the shower emitter onto the target. By using as the ion, for example, the silver ion or the zinc ion, it is possible to obtain on the target the antimicrobial effect peculiar to those ions. By using as the ion, for example, the copper ion, it is possible to exert on the target the antifungal effect peculiar to that ion.

By spraying, in the form of a shower, liquid droplets containing the silver or zinc ion having an antimicrobial effect or the copper ion having an antifungal effect into a space, it is possible to capture germs and mold floating in the space into liquid droplets and then deactivate them with those ions. Here, "deactivate" denotes exerting disinfecting, antimicrobial, sterilizing, decomposing, eliminating, and other effects. By spraying liquid droplets containing such an ion onto food, it is possible to prevent the rotting of the food and keep the food fresh.

As well as the silver, copper, and zinc ions, the nickel, palladium, platinum, rhodium, ruthenium, and other ions have an effect of retarding the aging and deterioration in freshness of plants caused by ethylene. Thus, by spraying liquid droplets containing such an ion on vegetables, fruits, and cut flowers, it is possible to keep them fresh.

(3) In the water feeding apparatus of the invention, the ion eluter may include an electrode from which a metallic ion is eluted and an outflow port through which the water is fed to the shower emitter, with the outflow port located in a position lower than the lower end of the electrode.

With this construction, even if metallic ion water remains inside the ion eluter, the remaining water is drained through the outflow port. Here, since the outflow port is located below the lower end of the electrode, the remaining water present above the outflow port is drained. That is, the electrode, which is located above the outflow port, is not dipped in the remaining water. This prevents the metallic ion contained in the remaining water from precipitating as metal or salts thereof and short-circuiting between electrodes.

(4) In the water feeding apparatus of the invention, the ion eluter may include an electrode from which a metallic ion is eluted and (a plurality of) outflow ports through which the water is fed to the shower emitter, the outflow ports including a first outflow port that is located in a position lower than the lower end of the electrode and a second outflow port that is located in a position higher than the higher end of the electrode.

With this construction, the air inside the ion eluter can be evacuated through the first outflow port, which is located above the upper end of the electrode. The ion eluter can contain water up to the position of the first outflow port, i.e., until the entire electrode is dipped in the water. This makes it possible to effectively use the electrode. In addition, the remaining water inside the ion eluter can be drained through the second outflow port, which is located below the lower end of the electrode. This prevents the electrode from being dipped in the remaining water, and thus prevents the metallic ion contained in the remaining water from precipitating as metal or salts thereof and short-circuiting between electrodes.

(5) In the water feeding apparatus of the invention, the shower emitter may be composed of a vibrator that atomizes by vibration the water fed thereto via the adder.

Where shower emission is used, to obtain small liquid droplets, it is necessary to use small holes (nozzles). Small holes are liable to cause water to stagnate inside the water passage, and may themselves be clogged with precipitate. Small holes are liable to cause water to stagnate also inside the adder, and may thus cause, in particular when the adder is provided with electrodes, precipitate to form and thereby short-circuit between the electrodes. To prevent this, it is necessary, for example, to provide a plurality of outflow ports. When high-concentration silver ion water is used, or when a treatment substance such as a high-viscosity starching agent is used, the small holes themselves may be clogged.

By contrast, where a vibrator is used to atomize water, there is no need to use small holes. This helps avoid the problems mentioned above. Moreover, simply by stopping the feeding of the signal to the vibrator, it is possible to stop atomizing silver ion water. This is convenient when silver ion water is collected in a container so as to be used for other purposes.

According to the present invention, a method of feeding water whereby shower water is sprayed onto a target to be fed with water uses the water feeding apparatus of claim 1.

By spraying shower water onto the target by the use of the water feeding apparatus of the invention, it is possible to quicken the drying of the liquid droplets attached to the surface of the target, and to make the treatment substance dissolved in the water precipitate and crystallize in a state that permits the treatment substance to be easily eluted when it meets water next time. This makes it easier for the treatment substance to exert the effect (for example, a antimicrobial effect) peculiar thereto that it exerts when eluted. Thus, it is possible to surely obtain the effect.

Moreover, the liquid droplets of shower water are small and have large surface areas, and are thus easier to dry. Thus, by spraying shower water onto the target, it is possible, irrespective of the type of the target (i.e., irrespective of whether the target is water-repellent or hydrophobic), to surely make water containing the treatment substance attach to the surface of the target. Thus, it is possible to obtain the above-described effect irrespective of the type of the target.

(7) According to the present invention, a washer is provided with: the water feeding apparatus of the invention described above; and a laundry tub in which laundry is put as the target to be fed with water.

In the washer constructed as described above, the water containing the treatment substance from the water feeding apparatus is sprayed, in the form of a shower, onto the laundry put in the laundry tub. In this way, it is possible to quicken the drying of the liquid droplets attached to the surface of the laundry, and make the treatment substance crystallize in a state that permits it to be easily eluted when it meets water next time. This makes it easier for the treatment substance to be eluted when it makes contact with water next time, and thus makes it easier for the treatment substance to exert the effect (for example, a antimicrobial effect or a softening effect) peculiar thereto. Thus, it is possible to surely obtain the effect on the laundry.

(8) The washer of the invention may be further provided with controlling means for controlling the addition of the treatment substance to the water by the adder in such a way that either first water containing the treatment substance or second water not containing the treatment substance is sprayed onto the laundry.

In the construction described above, under the control of the controlling means, either the first or second water can selectively be sprayed from the shower emitter onto the target. Thus, for example, it is possible to spray first the first water and then the second water onto the target. In this case, spraying the first water permits the treatment substance attach to the surface of the target, and then spraying the second water permits the treatment substance to seep deep into the target. Reversely, it is also possible to spray first the second water and then the first water onto the target. In this case, spraying the second water makes the target wet, and thereby makes it easier, when the first water is sprayed thereafter, for the treatment substance attached to the surface of the target to seep deep into the target. Thus, in either case, it is possible to obtain the effect (for example, an antimicrobial effect) exerted by the treatment substance uniformly all over the laundry.

(9) In the washer of the invention, the controlling means may be so configured as to perform control such that the shower emitter sprays the first water during at least one of a rinsing process, a spin-drying process, and a drying process.

With this construction, during at least one of a rinsing process, a spin-drying process, and a drying process, it is possible to apply the effect (for example, an antimicrobial effect) of the treatment substance contained in the first water to the laundry.

(10) In the washer of the invention, the controlling means may be so configured as to perform control such that the spraying of the first water by the shower emitter is turned on and off repeatedly during a drying process.

With this construction, while the first water is shower-sprayed onto the laundry a plurality of times, the first water sprayed at different times is dried quickly on a little-by-littlie basis. This makes it possible to produce crystals with still smaller particles and with still more lattice defects. This makes it easier for the treatment substance to be eluted, and thus makes it easier for the treatment substance to exert the effect thereof.

(11) In the washer of the invention, the controlling means may be so configured as to perform control such that the laundry is moved while the first water is being sprayed.

The laundry can be moved, for example, by rotating the laundry tub in which the laundry is put, or by rotating an agitating member (pulsator). This prevents the first water being sprayed from being kept sprayed onto the same place on the surface of the laundry. In this way, it is possible to spray the first water uniformly onto the target and thereby obtain the effect of the treatment substance uniformly all over the laundry.

(12) In the washer of the invention, the controlling means may be so configured as to perform control such that air is blown onto the laundry while the first water is being sprayed.

By blowing air onto the laundry while the first water is being sprayed, it is possible to more quickly dry the first water attached to the laundry. This makes it possible to surely produce crystals (treatment substance) with smaller particles and with more lattice defects. This makes it easier for the treatment substance to be eluted, and thus makes it easier for the treatment substance to exert the effect thereof.

(13) In the washer of the invention, the treatment substance may be a metallic ion.

For example, when the silver ion or the zinc ion is used as the metallic ion, it is possible to apply an antimicrobial effect to the laundry; when the copper ion is used as the metallic ion, it is possible to apply an antifungal effect to the laundry. That is, by using a metallic ion as the treatment substance, it is possible to apply to the laundry an antimicrobial effect or an antifungal effect peculiar to the given metallic ion.

(14) In the washer of the invention, the metallic ion may be a silver ion, and the amount of metal that is attached to the laundry sprayed with the first water containing the silver ion may be 0.1 mg or more per kilogram of laundry.

It has been experimentally found that, if the amount of attached metal is less than 0.1 mg per kilogram of laundry, when the washed laundry is left wet in an airtight space for a predetermined period of time, the laundry gives off foul odors. By contrast, when the amount of attached metal is 0.1 mg or more per kilogram of laundry as described above, the antimicrobial effect of the silver ion acts effectively, almost completely suppressing such foul odors.

(15) In the washer of the invention, the metallic ion may be a silver ion, and the amount of metal that is attached to the laundry sprayed with the first water containing the silver ion may be less than 19 mg per kilogram of laundry.

If the amount of attached metal (silver) is 19 mg or more per kilogram of laundry, it is possible to visually observe a lowering of the light reflectivity of the laundry as compared with when no metal is attached thereto. This means that attaching an excessive amount of metal results in the laundry being soiled with the metal. Accordingly, by limiting the amount of metal attached to the laundry to less than 19 mg per kilogram of laundry, it is possible to suppress the soil on the laundry ascribable to the silver attached thereto to a visually unobservable degree.

In the washer of the invention, the controlling means may be so configured as to control a drain valve for draining the water inside the laundry tub in such a way that the draining of water is suspended for a predetermined period of time after the shower emitter finishes spraying the shower water.

When shower water containing the treatment substance is sprayed onto the laundry (for example, cloth) put in the laundry tub, if the water is drained immediately thereafter, while the treatment substance readily attaches to the part of the cloth appearing at the surface, it may not attach to the part of the cloth located inside, because, under ordinary washing conditions, cloth is in a crumpled-up state.

To overcome this, the control means controls the drain valve, for example, in such a way that the drain valve is closed while the shower is being sprayed and the draining of water is suspended for a predetermined period of time after completion of the spraying of the shower, or in such a way that, after completion of the spraying of water in the form f a shower from the shower emitter, the drain valve is closed for a predetermined period of time to suspend the draining of water during this period. This permits cloth (in particular, the part thereof located inside) to surely absorb the treatment substance contained in the water remaining in the laundry tub.

(17) In the washer of the invention, the controlling means may be so configured as to perform control such that the laundry tub is rotated for a predetermined period of time after the shower emitter finishes spraying the shower water.

Suspending the draining of water for a predetermined period of time after completion of the spraying of the shower helps enhance the absorption of the treatment substance. However, if the laundry tub remains at rest, the water containing the treatment substance sprayed from the shower emitter collects, under gravity, in a bottom portion of the laundry tub. In the bottom portion of the laundry tub, there is provided an agitating member (pulsator) for agitating the laundry, and therefore, even when the drain valve is closed, the water collects below the pulsator, and thus does not always make contact with the cloth.

By contrast, when the controlling means rotates the laundry tub for the predetermined period of time as described above, the centrifugal force resulting from the rotation causes the water to rise upward, and thereby permits the water to make contact with the cloth. In this way, it is possible to attach more of the treatment substance to the cloth. Moreover, where the laundry tub is rotated in this way, the centrifugal force causes the water to rise upward, and thereby prevents the water from being drained through the drain valve located below. This eliminates the need to keep the drain valve closed.

(18) The washer of the invention may be further provided with: an input handler for accepting the setting of a washing course; and an operation controller for controlling the operation of the washing course set via the input handler. Here, the laundry tub is a holeless tub, and, when a tub cleaning course for cleaning the laundry tub is set as the washing course via the input handler, the operation controller controls the operation of the tub cleaning course in such a way that the tub is cleaned with an amount of water sufficient to permit an agitating member for agitating the laundry put in the holeless tub to be immersed in the water.

When a holeless tub is used as the laundry tub, the only part inside the laundry tub where the entry of mold is likely is around the agitating member (pulsator) for agitating the laundry. Accordingly, when the tub cleaning course is set via the input handler, by cleaning the tub, under the control of the operation controller, with an amount of water sufficient to permit the agitating member to be immersed in the water, it is possible to effectively clean the tub with a small amount of water. In this way, it is possible to suppress the proliferation of germs and mold inside the laundry tub and on the surface of the agitating member.

(19) In the washer of the invention, the operation controller may be so configured as to control the operation of the tub cleaning course in such a way that the tub is cleaned with water containing the metallic ion.

By cleaning the tub with water containing a metallic ion (for example, the silver ion or the copper ion), it is possible to effectively suppress the proliferation of germs and mold inside the laundry tub and on the surface of the agitating member.

Advantages of the Invention

As described above, according to the present invention, in an apparatus and a method for feeding water and a washer incorporating such an apparatus, liquid droplets having small particles that are easy to dry and that thus permit a treatment substance to be easily eluted as a result of the dissolution of crystals are generated and sprayed by a shower emitter onto a target to be fed with water. This makes it easy for the treatment substance to exert the effect thereof that it exerts when eluted. Thus, it is possible to surely obtain the effect peculiar to the treatment substance.

Moreover, even when the target is water-repellant or hydrophobic cloth, by spraying shower water onto the cloth, it is possible to surely make the treatment substance contained in the shower water attach to the surface of the cloth. Thus, even with a target, such as water-repellant or hydrophobic cloth, that the treatment substance is difficult to penetrate, it is possible to surely obtain the effect of the treatment substance that it exerts when eluted.

BRIEF DESCRIPTION OF DRAWINGS

[FIG. 11] A diagram illustrating the contents of the standard and antimicrobial treatment courses performed by the above washer;

Figure 1:
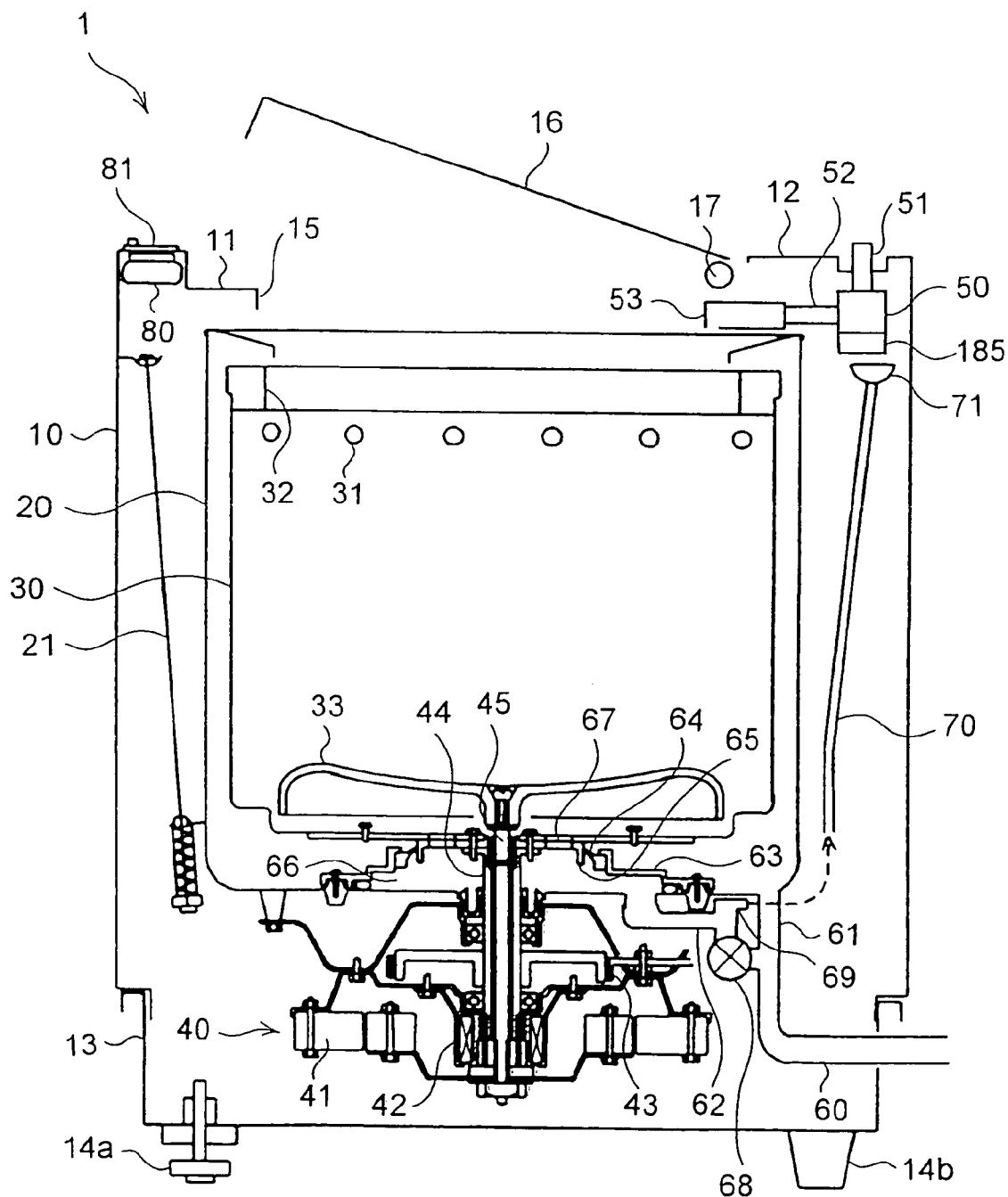
[FIG. 1] A sectional view showing an outline of the construction of a washer embodying the invention.

LIST OF REFERENCE SYMBOLS 1 washer
30 washing tub (placement tub)
80 control unit (control means)
100 ion elution unit (adder, ion eluter)
112 outflow port
112a outflow port
112b outflow port
113 electrode
114 electrode
120 drive circuit (control means)
200 shower emitter
200a shower emitter
200b shower emitter
300 water feeding apparatus
405 supersonic partial washing apparatus 405 (vibrator)

BEST MODE FOR CARRYING OUT THE INVENTION

Hereinafter, an embodiment of the present invention will be described with reference to FIGS. 1 to 16.

The most distinctive features of the present invention are as follows. Water containing a treatment substance is sprayed in the form of a shower onto a target to be fed with water so that small water particles (liquid droplets) attach to the surface of the target. This makes it easy for the water to dry, and also makes it easy for the treatment substance, which crystallizes when the water dries up, to dissolve into water again. This makes it easy for the treatment substance to exert the effect peculiar thereto. Now, the present invention will be described with emphasis placed on these features.

The target that is fed with water is, for example, any of the following. When a water feeding apparatus of the invention is used in a clothes washer, the target is laundry; when the water feeding apparatus is used in a dish washer-dryer, the target is tableware. When the water feeding apparatus is used in a shower apparatus installed in, for example, a bathroom or washroom, the target is one (human or animal) that is taking a bath or one who is washing his or her face; when the water feeding apparatus is used in a shower apparatus installed at a toilet, the target is a human (his or her buttocks). When the water feeding apparatus is used in a water sprinkling apparatus for gardening use, the target is plants in a garden.

A water feeding apparatus of the invention is for feeding water to a target as mentioned above, and can be used in a washer or a water spraying apparatus. Here, a water spraying apparatus is any apparatus that incorporates a water feeding apparatus of the invention and that makes it spray shower water to a target to be fed with water. Examples of water spraying apparatuses include, to name a few, dish washer-dryers, shower apparatuses, and water sprinkling apparatuses mentioned above.

A water feeding apparatus of the invention can be applied to any apparatus that feeds water to a target to be fed with water. As one example of such an apparatus, a washer incorporating a water feeding apparatus of the invention will be dealt with in the following descriptions.

(1. Construction of a Washer)

FIG. 1 is a vertical sectional view showing the overall construction of a washer 1. The washer 1 is of a full-automatic type, and has an exterior casing 10. The exterior casing 10 is rectangular in shape, is formed of metal or synthetic resin, and is open in the top and bottom faces thereof. Over the opening in the top face of the exterior casing 10 is laid a top face plate 11 made of synthetic resin, and this top face plate 11 is fastened to the exterior casing 10 with screws.

In FIG. 1, the front and rear faces of the washer 1 are shown on the left and right of the figure, respectively. Over a rear-end area of the top surface of the top face plate 11 is laid a back panel 12 made of synthetic resin, and this back panel 12 is fastened to the exterior casing 10 or the top face plate 11 with screws. Under the opening in the bottom face of the exterior casing 10 is laid a base 13 made of synthetic resin, and this base 13 is fastened to the exterior casing 10 with screws. In FIG. 1, all the screws thus far mentioned are omitted.

At the four corners of the base 13, there are provided feet 14a and 14b for supporting the exterior casing 10 on the floor.

The front-side feet 14*a* are screw feet of which the height can be adjusted. By rotating these, the washer 1 can be leveled. The rear-side feet 14*b* are formed integrally with the base 13 and have a fixed height.

In the top face plate 11 is formed a laundry inlet opening 15 through which to put laundry in a washing tub 30, which will be described later. A lid 16 is coupled to the top face plate 11 with a hinge 17. The lid 16 pivots in a vertical plane to cover the laundry inlet opening 15 from above.

Inside the exterior casing 10, there are arranged a water tub 20 and a washing tub 30 that is shared as a spin-drying tub. The water tub 20 and the washing tub 30 are each shaped like a cylindrical cup open at the top face thereof. The water tub 20 and the washing tub 30 are arranged concentrically with each other, with their axial lines vertically aligned, and with the former placed inside the latter.

The water tub 20 is suspended by suspension members 21. Four suspension members 21 in total are provided so as to link a lower portion of the exterior surface of the water tub 20 to interior corner portions of the exterior casing 10. Thus, the suspension members 21 hold the water tub 20 so that the water tub 20 can swing in a horizontal plane.

The washing tub 30 has a circumferential wall that is so tapered as to gradually widen upward. This circumferential wall has no holes, as permit passage of water, formed therein except a plurality of drain holes 31 arranged around the top-most portion thereof. That is, the washing tub 30 is of the so-called "holeless" type. Around the rim of the top opening of the washing tub 30, there is fitted a ring-shaped balancer 32. The balancer 32 serves to reduce the vibration that is produced when the washing tub 30 is rotated at high speed to spin-dry laundry. On the interior bottom surface of the washing tub 30, there is provided a pulsator 33 for producing a current of washing or rinsing water inside the tub.

On the exterior bottom surface of the water tub 20, a drive unit 40 is mounted. The drive unit 40 includes a motor 41, a clutch mechanism 42, and a brake mechanism 43. From a central portion of the drive unit 40 protrude upward a spin-dry spindle 44 and a pulsator spindle 45. The spin-dry spindle 44 and the pulsator spindle 45 have a double-spindle structure, with the former placed outside the latter. The spin-dry spindle 44, from bottom to top, penetrates the water tub 20, and then links to and thereby supports the washing tub 30. The pulsator spindle 45, from bottom to top, penetrates the water tub 20, then penetrates the washing tub 30, and then links to and thereby supports the pulsator 33. Sealing members for preventing leakage of water are provided between the spin-dry spindle 44 and the water tub 20 and between the spin-dry spindle 44 and the pulsator spindle 45.

In a space under the back panel 12, there is provided a feed valve 50 that is electromagnetically opened and closed. The feed valve 50 has a connection pipe 51 that penetrates the back panel 12 and protrudes upward. To the connection pipe 51 is connected a feed hose (not illustrated) by way of which clean water such as tap water is supplied. The feed valve 50 is connected also to a water server unit 53 shaped like a container. The water server unit 53 is so located as to face the inside of the washing tub 30, and is constructed as shown in FIG. 2.

Figure 2:
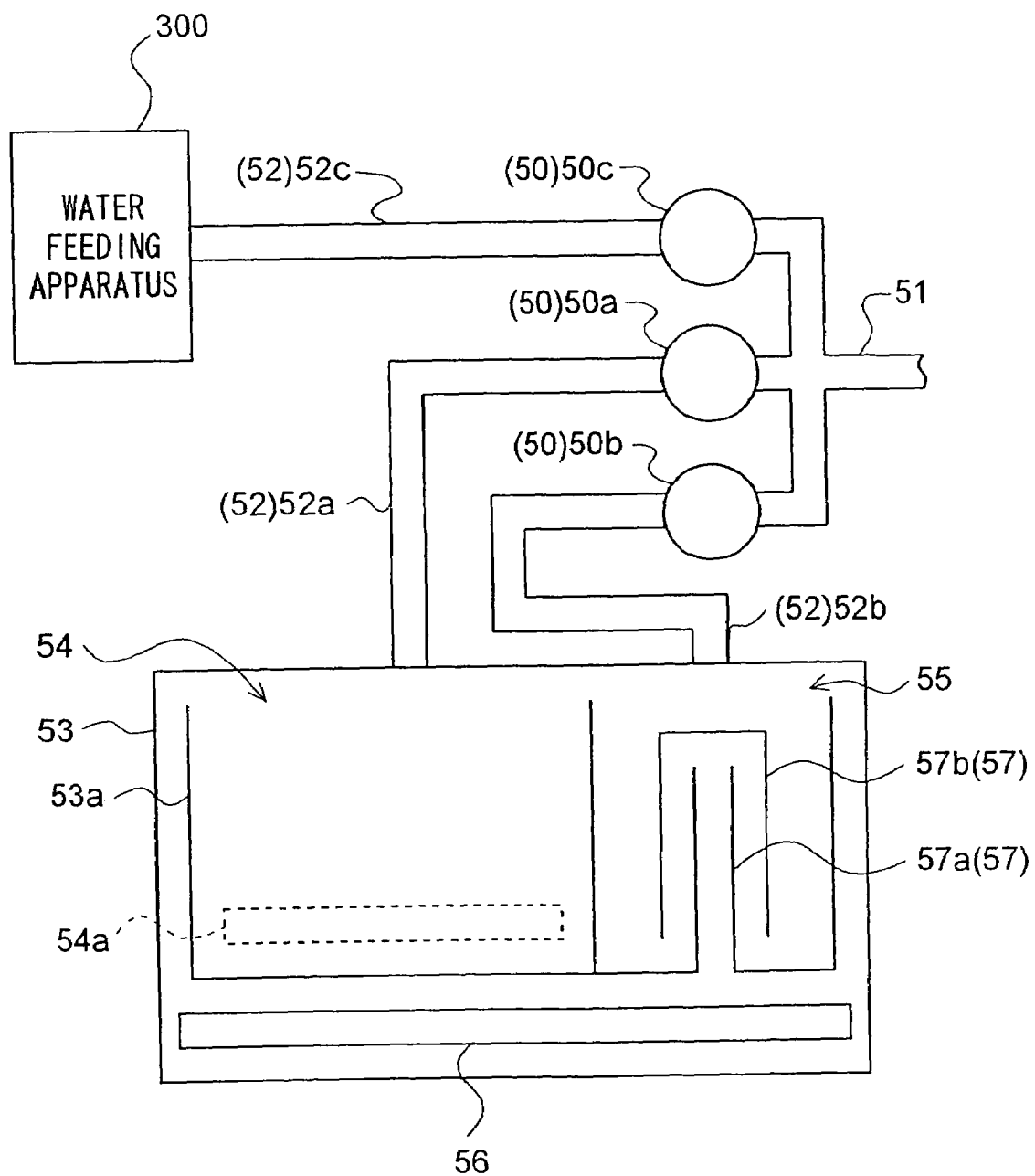
[FIG. 2] A sectional view schematically showing the construction of the water server unit of the above washer.

FIG. 2 is a vertical sectional view schematically showing the water server unit 53 as seen from the front face thereof. The water server unit 53 is open in the front face thereof, and in this opening is inserted a drawer 53*a* (adder case). The interior of the drawer 53*a* is divided into a plurality of compartments (in this embodiment, two, i.e., left-hand and right-hand, compartments). The left-hand compartment is a detergent compartment 54 used as a preparatory space for keeping detergent in. The right-hand compartment is a treatment agent compartment 55 used as a preparatory space for keeping a treatment agent in. In a bottom portion of the detergent compartment 54, there is formed a water outlet 54*a* that is open toward the interior of the water server unit 53. Inside the treatment agent compartment 55 is provided a siphon 57. In a portion of the water server unit 53 under the drawer 53*a*, there is formed a water outlet 56 through which water is fed into the washing tub 30.

The siphon 57 is composed of an inner pipe 57*a* that rises vertically from the bottom surface of the treatment agent compartment 55 and a cap-shaped outer pipe 57*b* that is fitted around the inner pipe 57*a*. Between the inner pipe 57*a* and the outer pipe 57*b* is formed a gap that permits passage of water. The inner pipe 57*a* is, at the bottom end thereof, open toward the bottom of the water server unit 53. The outer pipe 57*b* is located with a gap left between the bottom end thereof and the bottom surface of the treatment agent compartment 55 so that this gap serves as a water inlet. When water is fed into the treatment agent compartment 55 until the water level becomes higher than the top end of the inner pipe 57*a*, on the principle of a siphon, water is sucked out of the treatment agent compartment 55 through the siphon 57, and flows toward the bottom of the water server unit 53. From there, the water falls into the washing tub 30 through the water outlet 56.

The feed valve 50 is composed of a main feed valve 50*a*, a sub feed valve 50*b*, and a shower feed valve 50*c*. To these three feed valves is connected the connection pipe 51 at the end thereof at which it is divided into three branches. The water-in end of the connection pipe 51 is connected by way of a hose or the like to a facet of tap water.

The main feed valve 50*a* is connected via a main feed pipe 52*a* to an opening formed in the ceiling of the water server unit 53. This opening is open toward the detergent compartment 54. Accordingly, the water that flows out of the main feed valve 50*a* is fed via the main feed pipe 52*a* into the detergent compartment 54.

The sub feed valve 50*b* is connected via a sub feed pipe 52*b* to an opening formed in the ceiling of the water server unit 53. This opening is open toward the treatment agent compartment 55. Accordingly, the water that flows out of the sub feed valve 50*b* is fed via the sub feed pipe 52*b* into the treatment agent compartment 55. Thus, the route running from the main feed valve 50*a* via the detergent compartment 54 to the washing tub 30 is provided separately from the route running from the sub feed valve 50*b* via the treatment agent compartment 55 to the washing tub 30.

The shower feed valve 50*c* is connected via a shower feed pipe 52*c* to a water feeding apparatus 300 of the invention. The three feed pipes, namely the main feed pipe 52*a*, sub feed pipe 52*b*, and shower feed pipe 52*c*, together constitute a feed pipe 52.

Inside the connection pipe 51 is provided an unillustrated strainer. The strainer is for preventing foreign objects from entering the feed valve 50 and the water feeding apparatus 300.

Back in FIG. 1, to the bottom of the water tub 20 is fitted a drain hose 60 by way of which water inside the water tub 20 and the washing tub 30 is drained out of the exterior casing 10. Water flows into the drain hose 60 from drain pipes 61 and 62. The drain pipe 61 is connected to the bottom surface of the water tub 20, at a place near the circumference thereof. The drain pipe 62 is connected to the bottom surface of the water tub 20, at a place near the center thereof.

A ring-shaped partition wall 63 is fixed on the interior bottom surface of the water tub 20 so as to enclose the portion thereof to which the drain pipe 62 is connected. In an upper portion of the partition wall 63 is fitted a ring-shaped sealing member 64. This sealing member 64 makes contact with a disk 65 fixed on the exterior bottom surface of the washing tub 30, and thereby forms a separate drain space 66 between the water tub 20 and the washing tub 30. The drain space 66 connects via a drain outlet 67 formed in the bottom of the washing tub 30 to the interior of the washing tub 30.

The drain pipe 62 is fitted with a drain valve 68 that is electromagnetically opened and closed. In a portion of the drain pipe 62 located on the upstream side of the drain valve 68, there is provided an air trap 69. From the air trap 69 extends a lead pipe 70. To the upper end of the lead pipe 70 is connected a water level switch 71 that serves as a means for detecting the water level inside the washing tub 30 or the water tub 20.

In a front-side portion of the exterior casing 10, there is provided a control unit 80. The control unit 80 is located beneath the top face plate 11. The control unit 80 receives operation instructions from the user via an operation/display unit 81 provided on the top surface of the top face plate 11, and feeds operation commands to the drive unit 40, feed valve 50, and drain valve 68. The control unit 80 also feeds display commands to the operation/display unit 81. The control unit 80 includes a control circuit 120 (see FIG. 10) for driving an ion elution unit 100, which will be described later.

On the downstream side of the main feed valve 50a with respect to the water feed route, there is provided a flow rate detecting means 185. The flow rate detecting means 185 is realized with a conventionally known flowmeter. In FIG. 1, the flow rate detecting means 185 is illustrated as attached to the feed valve 50. It is, however, also possible to provide it elsewhere, for example at the ion elution unit 100 described later, or at the water server unit 53. The flow rate may be detected through calculations based on the variation per unit time in the flow rate of water as detected by the water level switch 71, or based on the time required for a predetermined variation in the flow rate of water to take place, or the like. Instead of detecting the flow rate, it is also possible to limit the flow rate within a certain range by using a valve that permits the flow rate to vary only within the certain range under ordinary water feed pressure.

(2. Operation of the Washer)

Next, the normal washing operation of the washer 1 will be described.

(2-1. Preparatory Operation of the Washer)

First, the lid 16 is opened, and laundry is put in the washing tub 30 through the laundry inlet opening 15. Then, the drawer 53a is pulled out of the water server unit 53, and detergent is put in the detergent compartment 54. As necessary, a treatment agent is put in the treatment agent compartment 55 of the water server unit 53. The treatment agent may be put in in the middle of a washing procedure, or, if unnecessary, may be dispensed with. With the detergent and the treatment agent put in, the drawer 53a is pushed back into the water server unit 53. In a case where there is provided a means for detecting the volume of laundry, the detergent and the treatment agent may be put in, after the detection thereof, according to the magnitude of load, the amount of detergent, and the amount of water as estimated from the detected volume of laundry.

With the detergent and the treatment agent ready to be added, the lid 16 is closed, and the operation buttons on the operation/display unit 81 are appropriately operated to select desired washing conditions (a desired washing course). When a start button is pressed, selected processes are performed according to the flow charts shown in FIGS. 3 to 6.

The washing courses that the washer 1 can perform are divided roughly into normal courses and a tub cleaning course. The tub cleaning course is for cleaning at least one of the washing tub 30 and the water tub 20. One of those washing courses can be selected via the operation/display unit 81. Each washing course includes, as a washing procedure, at least one of washing, rinsing, spin-drying, and drying processes, which will be described later, or a combination of those processes.

The normal courses mentioned above are further divided into standard courses and antimicrobial treatment courses.

The standard courses are for washing laundry, and include a soft course, a powerful course, a dry course, a blanket course, and other courses to cope with different types of laundry. Different settings can be made for each of these courses, and thus, according to which of those courses are selected, at least one of washing, rinsing, spin-drying, and drying processes is selected and performed as a washing procedure. The different courses differ from one another, depending on their respective purposes, in the durations for which the washing, rinsing, spin-drying, and drying processes are respectively performed, the rotation rate (agitation force), and other parameters.

The antimicrobial treatment courses are for treating laundry with antimicrobial treatment. When an antimicrobial treatment course is selected on the operation/display unit 81, a washing procedure is performed that is basically the same as the one performed when a standard course is selected on the operation/display unit 81. The only difference is that, in the middle of the procedure (for example, during the rinsing process), a metallic ion is eluted from the ion elution unit 100 (see FIG. 7), and water containing the metallic ion is fed from a shower emitter 200 (see FIG. 7), which will be described later, into the washing tub 30. Thus, laundry is treated with antimicrobial treatment. The antimicrobial treatment courses will be described in detail later.

(2-2. Basic Operation Performed in a Standard Course)

Figure 3:
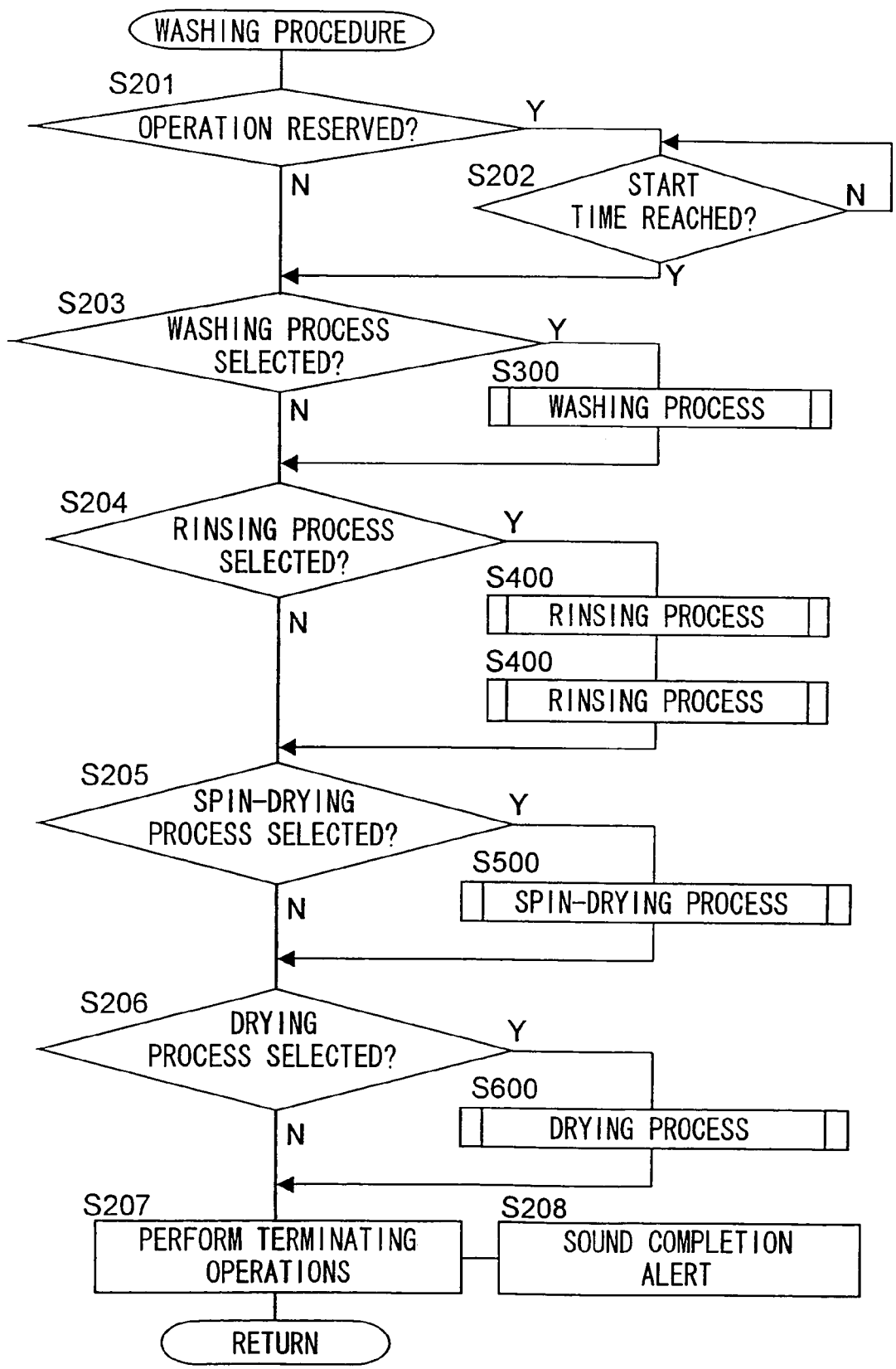
[FIG. 3] A flow chart showing the flow of operations performed through an entire washing procedure in the above washer.

Next, with reference to FIG. 3, a description will be given of the basic operation that the washer 1 performs when a standard course is selected as a washing course of the washer 1. FIG. 3 is a flow chart showing the flow of operations performed through an entire washing procedure. It should be noted that the various judgments mentioned in the following description are made by the control unit 80.

In step S201, whether or not operation is reserved, i.e., whether or not washing is programmed to start at a specified time, is checked. If operation is reserved, the operation flow proceeds to step S202; if not, the operation flow proceeds to step S203.

In step S202, whether or not the operation start time has reached is checked. When the operation start time has reached, then the operation flow proceeds to step S203.

In step S203, whether or not a washing process is selected is checked. If a washing process is selected, the operation flow proceeds to step S300; if not, the operation flow proceeds directly to step S204. The contents of the washing process in step S300 will be described later with reference to the flow chart shown in FIG. 4. On completion of the washing process in step S300, the operation flow proceeds to step S204.

In step S204, whether or not a rinsing process is selected is checked. If a rinsing process is selected, the operation flow proceeds to step S400; if not, the operation flow proceeds directly to step S205. The contents of the rinsing process in step S400 will be described later with reference to the flow chart shown in FIG. 5. On completion of the rinsing process in step S400, the operation flow proceeds to step S205.

In step S205, whether or not a spin-drying process is selected is checked. If a spin-drying process is selected, the operation flow proceeds to step S500; if not, the operation flow proceeds directly to step S206. The contents of the spin-drying process in step S500 will be described later with reference to the flow chart shown in FIG. 6. On completion of the spin-drying process in step S500, the operation flow proceeds to step S206.

In step S206, whether or not a drying process is selected is checked. If a drying process is selected, the operation flow proceeds to step S600; if not, the operation flow proceeds directly to step S207. In the drying process in step S600, laundry is dried, for example, by sending warm air into the washing tub 30. The warm, humid air discharged out of the washing tub 30 is cooled by cooling water (water cooling dehydration) so that the moisture contained in the air is converted into water, and is then discharged out of the washer. On completion of the drying process in step S600, the operation flow proceeds to step S207.

In step S207, the control unit 80, in particular the processing device (microcomputer) included therein, automatically performs a predetermined sequence of terminating operations. Then, in step S208, the control unit 80 sounds a completion alert to indicate the completion of the washing procedure. On completion of the entire procedure, the washer 1 is brought into a stand-by state in preparation for the next washing procedure.

(2-2-1. Washing Process)

Figure 4:
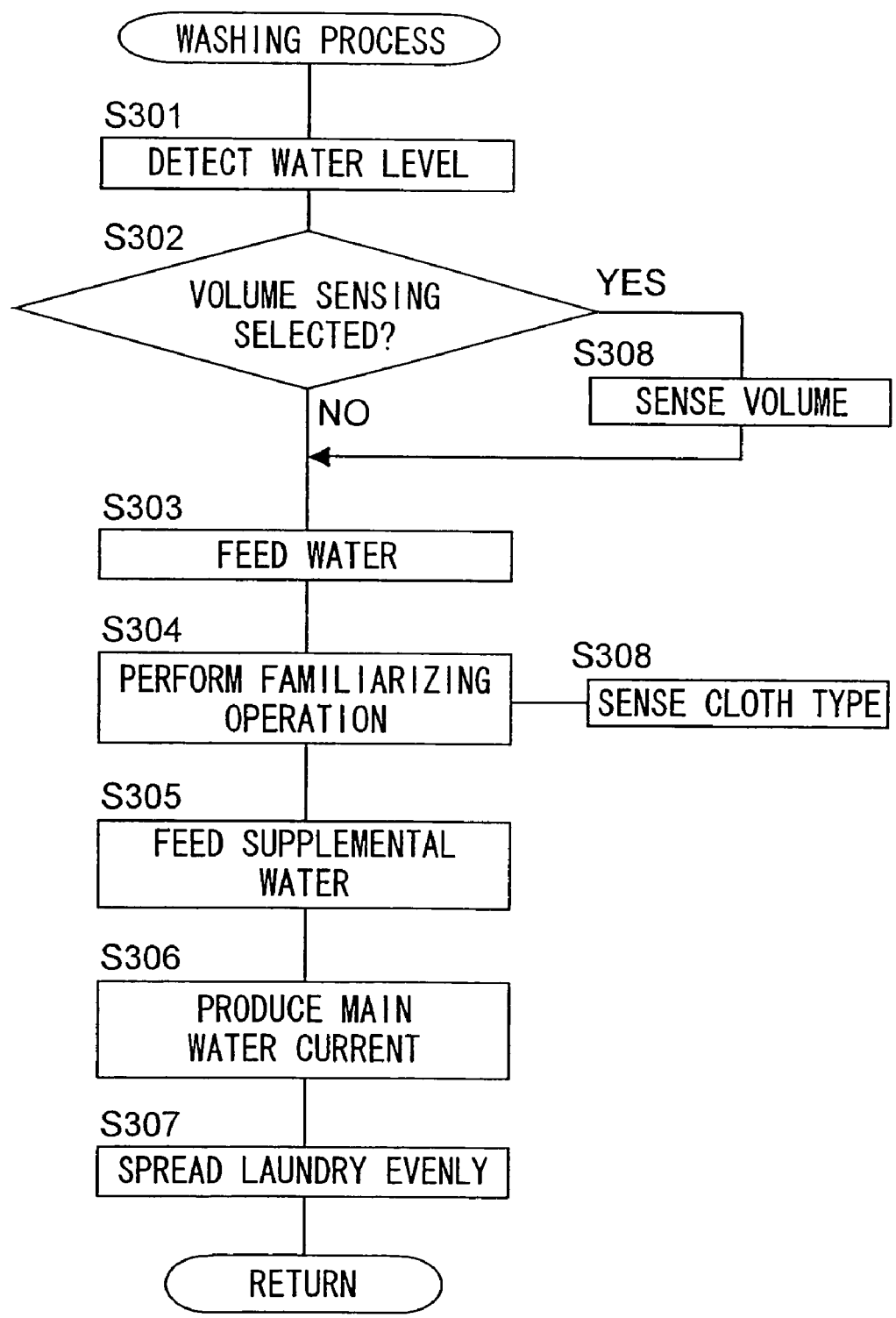
[FIG. 4] A flow chart showing the flow of operations performed in the washing process in the above washing procedure.

Next, the washing process mentioned above will be described in detail with reference to FIG. 4. FIG. 4 is a flow chart showing the flow of operations performed in the washing process. It should be noted that the various judgments mentioned in the following description are also made by the control unit 80.

In step 301, the data of the water level inside the washing tub 30 as detected by the water level switch 71 is referred to. In step S302, whether or not the sensing of the volume of laundry is selected is checked. If the sensing of the volume of laundry is selected, the operation flow proceeds to step S308; if not, the operation flow proceeds directly to step S303.

In step S308, on the basis of the rotation load of the pulsator 33, the volume of the laundry is measured. After the sensing of the volume, the operation flow proceeds to step S303.

In step S303, the main feed valve 50a is opened, and water is fed via the main feed pipe 52a and the water server unit 53 into the washing tub 30. At this time, mixed with the water, the detergent put in the detergent compartment 54 of the water server unit 53 is put in the washing tub 30. At this time point, the drain valve 68 is closed. When the water level switch 71 detects that the set water level is reached, the main feed valve 50a is closed, and the operation flow proceeds to step S304.

In step S304, familiarizing is performed. Specifically, the pulsator 33 is rotated alternately in the forward and reverse directions to agitate laundry and water to familiarize them with each other. This permits the laundry to absorb sufficient water. Moreover, it is also possible to permit the air caught in different parts of the laundry to escape. If, as a result of the familiarizing, the water level as detected by the water level switch 71 becomes lower than the original level, then, in step S305, the main feed valve 50a is opened to feed supplemental water so that the set water level is restored.

At this time, if the selected washing course includes "cloth type sensing", at the same time that the familiarizing is performed, the sensing of the cloth type is also performed. At the end of the familiarizing, how the water level has varied from the set water level is detected, and, if the drop in the water level is greater than a prescribed value, the cloth type is judged to be highly water-absorbing one.

When, in step S305, the set water level is obtained, the operation flow proceeds to step S306. In step S306, in accordance with the settings made by the user, the motor 41 rotates the pulsator 33 with a predetermined pattern to form, inside the washing tub 30, a main water current for washing. With this main water current, the laundry is washed. The brake mechanism 43 applies a brake to the spin-dry spindle 44 so that, even when the washing water and laundry move, the washing tub 30 does not rotate.

At the end of the period of the main water current, the operation flow proceeds to step S307. In step S307, the pulsator 33 rotates intermittently to make the laundry loose so that the laundry is spread evenly inside the washing tub 30. This is done in preparation for the spin-drying rotation of the washing tub 30.

(2-2-2. Rinsing Process)

Figure 5:
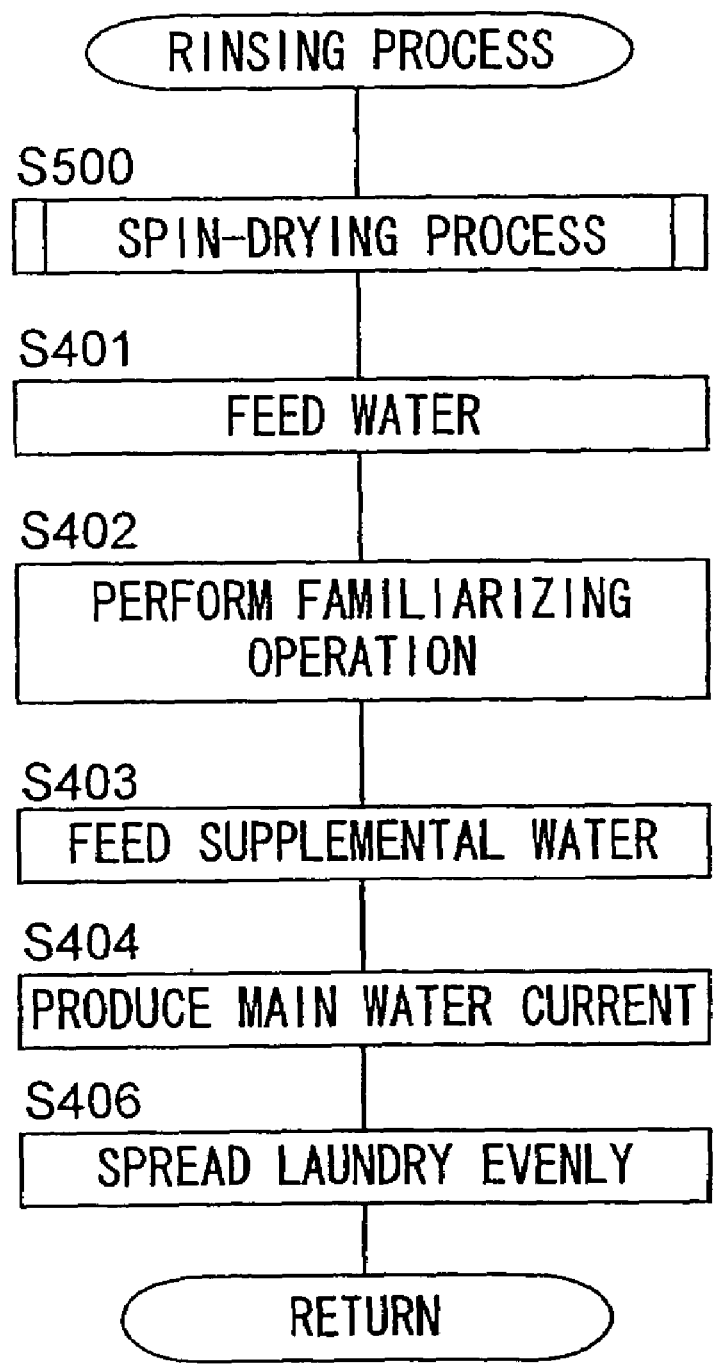
[FIG. 5] A flow chart showing the flow of operations performed in the rinsing process in the above washing procedure.

Next, the rinsing process mentioned above will be described in detail with reference to FIG. 5. FIG. 5 is a flow chart showing the flow of operations performed in the rinsing process. It should be noted that the various judgments mentioned in the following description are also made by the control unit 80.

First, in step S500, a spin-drying process is performed. This process will be described later with reference to the flow chart shown in FIG. 6. After this spin-drying process, the operation flow proceeds to step S401. In step S401, the main feed valve 50a is opened, and water is fed up to the set water level. If the addition of a treatment agent is selected, the sub feed valve 50b is also opened, and water is fed also by way of this route so that the treatment agent is put in the washing tub 30 via the siphon 57 and the water outlet 56.

After the feeding of water the operation flow proceeds to step S402. In step S402, familiarizing is performed. During this familiarizing, the laundry that has stuck to the washing tub 30 in step S500 (spin-drying process) is made loose therefrom, and is familiarized with water so as to absorb sufficient water.

After the familiarizing, the operation flow proceeds to step S403. If, as a result of the familiarizing, the water level as detected by the water level switch 71 becomes lower than the original level, then the main feed valve 50a is opened to feed supplemental water so that the set water level is restored.

After, in step S403, the set water level is restored, the operation flow proceeds to step S404. In step S404, in accordance with the settings made by the user, the motor 41 rotates the pulsator 33 with a predetermined pattern to form, inside the washing tub 30, a main water current for rinsing. With this main water current, the laundry is agitated, and is thereby rinsed. The brake mechanism 43 applies a brake to the spin-dry spindle 44 so that, even when the rinsing water and laundry move, the washing tub 30 does not rotate.

At the end of the period of the main water current, the operation flow proceeds to step S405. In step S405, the pulsator 33 rotates intermittently to make the laundry loose. This permits the laundry to be spread evenly inside the washing tub 30 in preparation for the spin-drying rotation.

In the above description, rinsing is performed as "stored-water rinsing" whereby rinsing is performed with rinsing water stored in the washing tub 30. It is, however, also possible to perform rinsing as "supplied-water rinsing" whereby rinsing is performed with fresh water kept being fed in, or as "shower rinsing" whereby water is sprayed onto the laundry from the water server unit 53 while the washing tub 30 is kept rotating at low speed.

(2-2-3. Spin-Drying Process)

Figure 6:
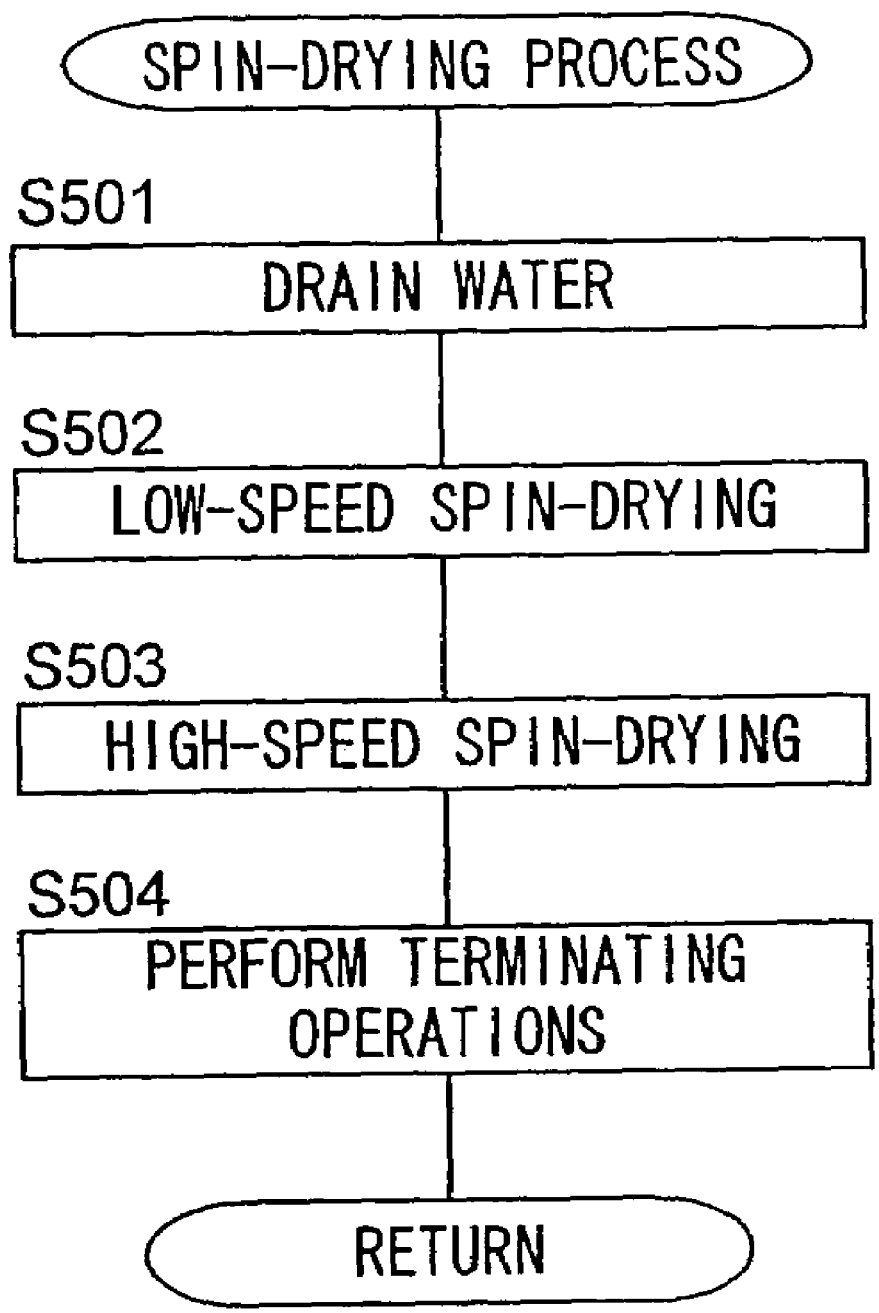
[FIG. 6] A flow chart showing the flow of operations performed in the spin-drying process in the above washing procedure.

Next, the spin-drying process mentioned above will be described in detail with reference to FIG. 6. FIG. 6 is a flow chart showing the flow of operations performed in the spin-drying process. It should be noted that the various judgments mentioned in the following description are also made by the control unit 80.

First, in step S501, the drain valve 68 is opened. Thus, the washing water inside the washing tub 30 is drained via the drain space 66. The drain valve 68 is kept open during the spin-drying process.

Then, in step S502, spin-drying is performed at comparatively low speed, and then, in step S503, spin-drying is performed at high speed. Then, in step S504, the supply of electric power to the motor 41 is stopped, and terminating operations, such as the application of a brake, is performed.

In the spin-drying process in steps S502 and S503, the following operations are performed. When most of the washing water has been drained out of the washing tub 30 and the laundry, the clutch mechanism 42 and the brake mechanism 43 are switched. The clutch mechanism 42 and the brake mechanism 43 may be switched before the starting of or at the same time as the draining of water. Now, the motor 41 rotates the spin-dry spindle 44. This causes the washing tub 30 to rotate for spin-drying. At this time, the pulsator 33 rotates along with the washing tub 30.

As the washing tub 30 rotates, the laundry is pressed onto the interior circumferential wall of the washing tub 30 under centrifugal force. Thus, the washing water contained in the laundry collects on the interior surface of the circumferential wall of the washing tub 30. At this time, since the washing tub 30 is so tapered as to gradually widen upward as described earlier, the washing water acted upon by the centrifugal force rises along the interior surface of the washing tub 30. When the washing water reaches the upper end of the washing tub 30, it is discharged through the drain holes 31. After leaving the drain holes 31, the washing water hits the interior surface of the water tub 20, and then flows along the interior surface of the water tub 20 to the bottom of the water tub 20. Then, the washing water is discharged out of the exterior casing 10 via the drain pipe 61 and the drain hose 60 connected thereto.

(3. Construction of the Water Feeding Apparatus)

Next, the water feeding apparatus 300, which is the most characteristic part of the present invention, will be described.

Figure 7:
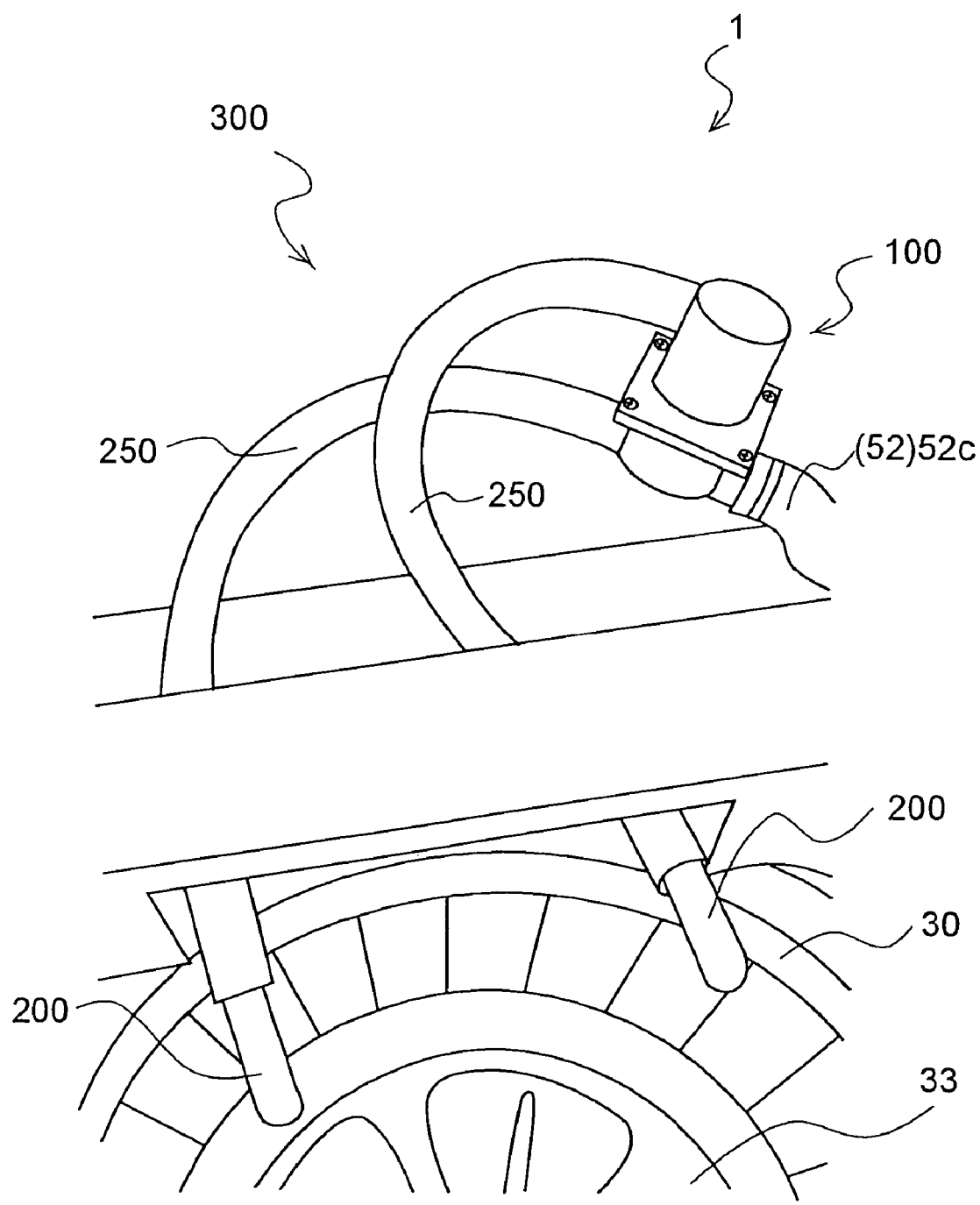
[FIG. 7] A perspective view, as seen obliquely from above, of the above washer fitted with a water feeding apparatus embodying the invention.
Figure 8:
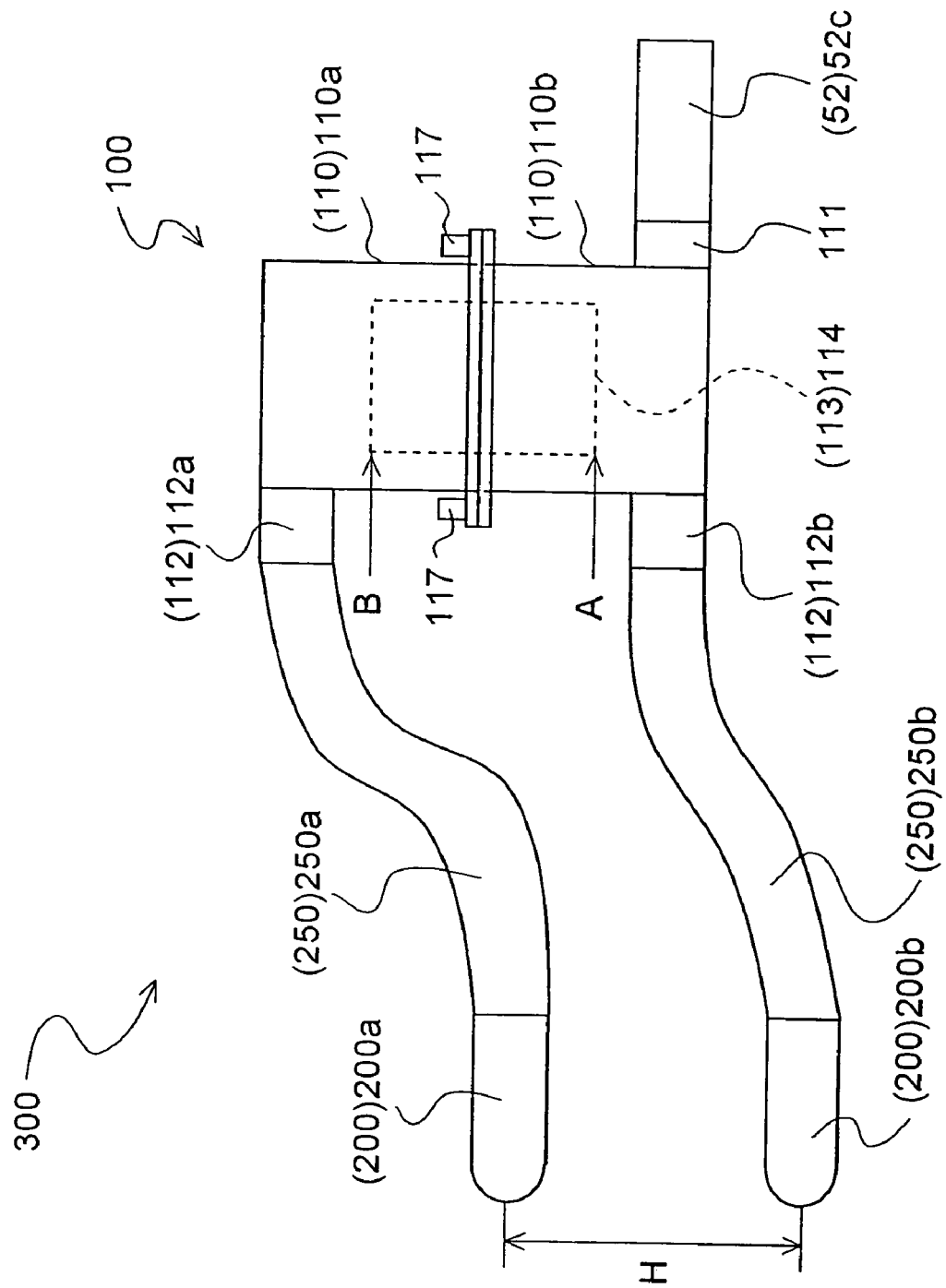
[FIG. 8] A side view schematically showing an outline of the construction of the above water feeding apparatus.

FIG. 7 is a perspective view, as seen obliquely from above, of the washer 1 fitted with the water feeding apparatus 300. FIG. 8 is a side view schematically showing the water feeding apparatus 300. The water feeding apparatus 300 is an apparatus for feeding water to laundry as a target to be fed with water, and has an ion elution unit 100 and a shower emitter 200. The ion elution unit 100 and the shower emitter 200 are connected together by a linking pipe 250.

(3-1. Construction of the Ion Elution Unit)

The ion elution unit 100 serves both as an adder for adding a treatment agent to the water that is fed from the shower feed pipe 52c to the laundry as the target and as an ion eluter that elutes, as the treatment agent, a metallic ion so that the metallic ion is added to the water that passes therethrough. The ion elution unit 100 has a casing 110, an inflow port 111, an outflow port 112, electrodes 113 and 114, and terminals 115 and 116 (see FIG. 9).

The casing 110 houses the electrodes 113 and 114 inside it, and is made of an insulating material such as synthetic resin, silicon, or rubber. The casing 110 is composed of an upper casing 110a and a lower casing 110b fastened together at several places with screws.

The casing 110 has a circular cross section along a certain plane, and has a substantially cylindrical shape as a whole. Giving the casing 110 this shape helps make the ion elution unit 100 pressure-resistant. More specifically, to permit the shower emitter 200, which will be described later, to spray a shower, the shower emitter 200 is provided with a narrowed nozzle, and this produces a high pressure inside the casing 110 of the ion elution unit 100. When the casing 110 is given a substantially cylindrical shape, such an internal pressure is distributed uniformly around the circumference thereof, resulting in resistance to the internal pressure. In this way, it is possible to prevent the destruction of the ion elution unit 100 ascribable to the internal pressure.

The shape of the casing 110 is not limited to a substantially cylindrical shape as specifically described above. Even with, for example, an elliptic, spherical, or spheroidal shape, it is possible to easily realize a pressure-resistant structure.

The inflow port 111 is an inlet for water through which water is fed from the shower feed pipe 52c into the casing 110. Thus, through this inflow port 111, water flows into the casing 110.

The outflow port 112 is an outlet for water through which water flows out of the casing 110 to the shower emitter 200. The water inside the casing 110 is fed via the outflow port 112 and the linking pipe 250 to the shower emitter 200. For the draining of the water remaining inside the casing 110, it is preferable to provide a plurality of outflow ports 112. In this embodiment, two outflow ports 112a and 112b are provided. How the outflow ports 112a and 112b are located relative to each other will be described later.

Figure 9:
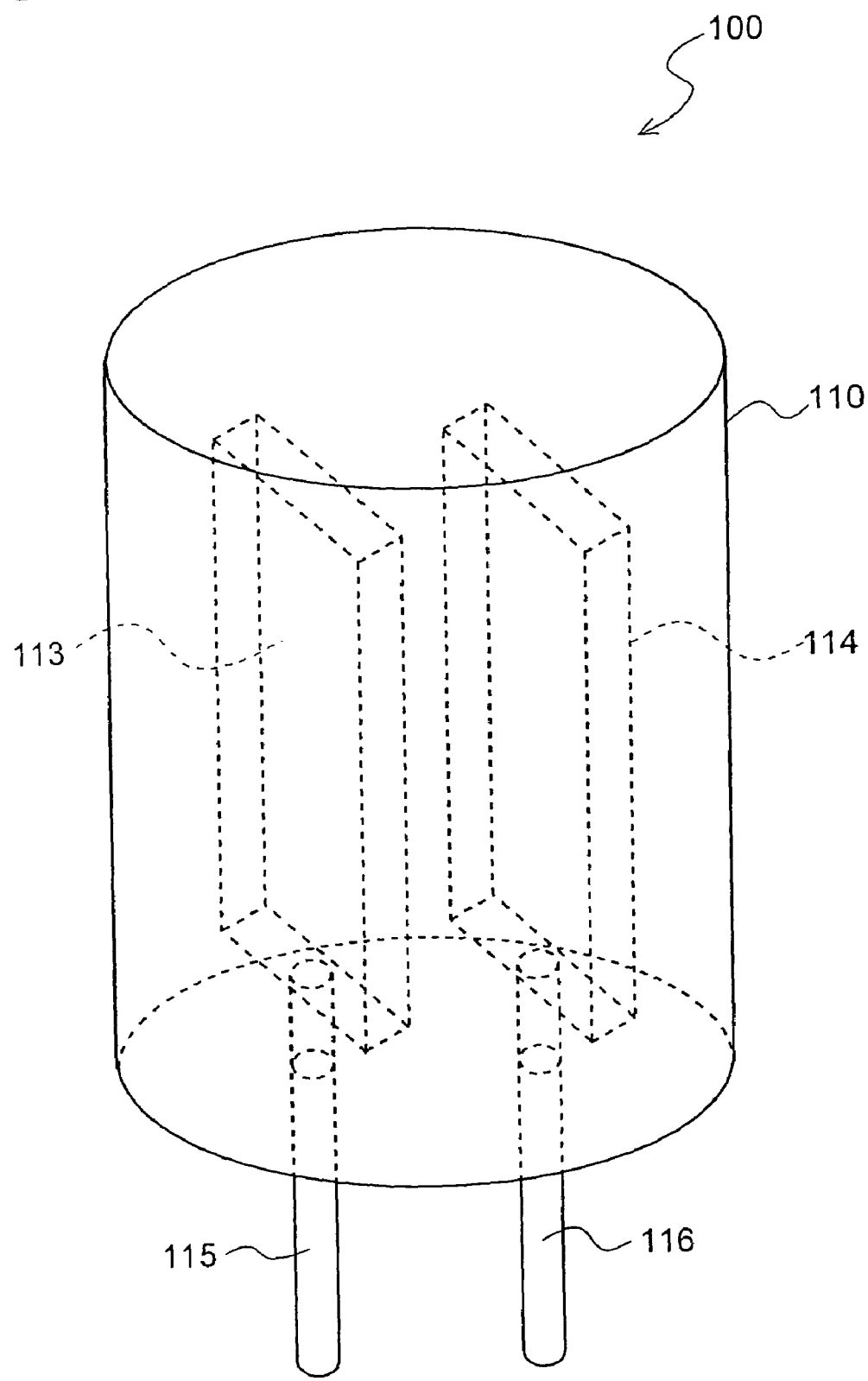
[FIG. 9] A perspective view schematically showing the exterior appearance and internal construction of the ion elution unit of the above water feeding apparatus.

The electrodes 113 and 114 are for eluting a metallic ion. FIG. 9 is a perspective view schematically showing the exterior appearance and internal construction of the ion elution unit 100. In this figure, for convenience sake, the inflow port 111 and the outflow port 112 are omitted. The electrodes 113 and 114 are each flat-plate-shaped, and are arranged parallel to and at a predetermined interval from each other inside the casing 110. When a voltage is applied between these two electrodes 113 and 114 via the terminals 115 and 116, which will be described later, for example, at the positive electrode, the metal of which the electrode is made is eluted, and is added to the water inside the casing 110.

It is preferable that the electrodes 113 and 114 be made of silver, copper, zinc, or an alloy thereof. The silver ion eluted from silver electrodes and the zinc ion eluted from zinc electrodes exert an excellent antimicrobial effect; the copper ion eluted from copper electrodes exerts an excellent antifungal effect. From an alloy of these metals, the ions of the ingredient metals can be eluted simultaneously. This makes it possible to obtain excellent antimicrobial and antifungal effects.

Specifically, when silver electrodes are used as the electrodes 113 and 114, an antimicrobial effect is obtained by the following mechanism.

For example, when a person sweats, the clothes smell as a result of the proliferation of germs. Inherently, sweat is odorless, and contains glycerides, which are esters of glycerin with fatty acids. Germs decompose these glycerides, with the result that the fatty acids separated therefrom give off odors.

When silver electrodes are used as the electrodes 113 and 114, by applying a voltage between those electrodes, it is possible to cause, at the positive electrode, the reaction $Ag \rightarrow Ag^+ + e^-$ and thereby elute the silver ion into water. This silver ion acts upon and deactivate the germs that cause odors. Thus, the glycerides contained in sweat are no longer decomposed. In this way, it is possible to suppress the generation of odors. Here, "deactivate" denotes exerting disinfecting, antimicrobial, sterilizing, decomposing, eliminating, and other effects.

The terminals 115 and 116 are for applying a voltage to the electrodes 113 and 114. The electrode 113 and the terminal 115 are made of the same metal (for example, silver), and the electrode 114 and the terminal 116 are made of the same metal (for example, silver). The terminals 115 and 116 penetrate the casing 110 from outside it so as to be electrically connected to the electrodes 113 and 114. The terminals 115 and 116 located outside the casing 110 are connected to a drive circuit 120 (see FIG. 10), which will be described later, provided in the control unit 80.

In this embodiment, the terminals 115 and 116 are given a cylindrical shape. This helps achieve enhanced sealing, where the terminals 115 and 116 penetrate the casing 110, between the terminals 115 and 116 and the casing 110.

More specifically, a high internal pressure resulting from the spraying of a shower is present inside the casing 110, and giving the terminals 115 and 116 a cylindrical shape, i.e., a circular cross section, helps distribute the high pressure uniformly around the circumference of the terminals 115 and 116. In this way, it is possible to prevent the destruction of the terminals 115 and 116, and to achieve enhanced sealing between the terminals 115 and 116 and the casing 110.

To obtain the above-mentioned effects, the terminals 115 and 116 need to have a circular cross section at least in the parts thereof where they penetrate the casing 110. However, giving the terminals 115 and 116 a circular cross section all over the axial length thereof as in this embodiment makes it easy to produce the terminals 115 and 116, and thus helps enhance the productivity of the ion elution unit 100.

The terminal 115 and the electrode 113, and the terminal 116 and the electrode 114, may be formed integrally. However, it is difficult to integrally form the terminal 115 or 116, which is cylindrically shaped, and the electrode 113 or 114, which is flat-plate-shaped. Accordingly, in this embodiment, the terminals 115 and 116 are silver-brazed and thereby electrically connected to the electrodes 113 and 114, respectively. Here, silver-brazing denotes cementing a metal part to a base material by using a molten brazing alloy, such as an alloy of silver and tin, that melts at a temperature lower than the melting point of the base material and thus without melting the base material.

Next, how the plurality of outflow ports 112 mentioned above are located relative to each other will be described.

After water is fed to the target to be fed with water, if water containing the metallic ion remains inside the casing 110 of the ion elution unit 100, the metallic ion may precipitate as metal or salts thereof, causing short-circuiting between the electrodes 113 and 114. On the other hand, if air remains inside the casing 110 of the ion elution unit 100, when water flows into the casing 110 next time, the remaining air prevents the electrodes 113 and 114 inside the casing 110 from being dipped in water up to the upper parts thereof. This makes it impossible to elute the metallic ion from the upper parts of the electrodes that are not dipped in water.

To avoid these inconveniences, in this embodiment, as shown in FIG. 8, the casing 110 of the ion elution unit 100 is provided with a plurality of outflow ports 112a and 112b that are located at different heights. Specifically, the outflow port 112a is located in a position higher than the outflow port 112b. The outflow port 112a is connected via the linking pipe 250 (250a) to the shower emitter 200 (200a), and the outflow port 112b is connected via the linking pipe 250 (250b) to the shower emitter 200 (200a).

As a result, even when metallic ion water remains inside the casing 110, the remaining water can be discharged out of the casing 110 via the outflow port 112b, located in a lower position, and then via the linking pipe 250b and the shower emitter 200b. On the other hand, even when air remains inside the casing 110 when water flows into the ion elution unit 100, the air may be exhausted out of the casing 110 via the outflow port 112a, located in a higher position, and then via linking pipe 250a and the shower emitter 200a. Thus, the level of the water that flows into the casing 110 can be raised at least up to the position of the outflow port 112a. In this way, it is possible to effectively use the electrodes 113 and 114 inside the casing 110 while avoiding short-circuiting between the electrodes 113 and 114 ascribable to the metallic ion contained in the remaining water.

Here, it is preferable that the outflow port 112b (first blowout port) located in the lower position be located in a position lower than the lower ends A of the electrodes 113 and 114 of the ion elution unit 100. This permits the portion of the water remaining inside the casing 110 that is located above the outflow port 112b to be discharged through the outflow port 112b, and thus helps surely prevent the entire electrodes 113 and 114 from being dipped in the remaining water. In this way, it is possible to surely prevent short-circuiting between the electrodes 113 and 114.

After the spraying of metallic ion water, either water containing no metallic ion or water containing a low concentration of the metallic ion may be sprayed in a predetermined amount or for a predetermined period of time. This helps lower the concentration of the metallic ion in the water that passes through the unit last. Thus, even when water remains inside the unit, since the remaining water contains a low concentration of the metallic ion, short-circuiting between the electrodes 113 and 114 ascribable to the metallic ion contained in the remaining water is less likely.

Moreover, in this embodiment, the outflow port 112b located in the lower position is so located as to make contact with the lower surface of the ion elution unit 100, meaning that the lowest part of the outflow port 112b is at the same level as the lower surface of the ion elution unit 100. This permits almost all of the water remaining inside the casing 110 to be discharged through the outflow port 112b. Thus, in addition to the above-mentioned effect of preventing short-circuiting between the electrodes 113 and 114, it is also possible to prevent inconveniences resulting from the freezing of the remaining water, specifically the deformation or destruction of the casing 110, the obstruction of the flow of water due to clogging inside the casing 110, and the like.

Moreover, in this embodiment, the outflow port 112a (second outflow port) located in the upper position is located in a position higher than the upper ends B of the electrodes 113 and 114 of the ion elution unit 100. Thus, even when air remains inside the casing 110 when water flows into the ion elution unit 100, it is possible to discharge the air out of the casing 110 through the outflow port 112a. Accordingly, the level of the water that flows into the ion elution unit 100 can be raised at least to that position. This permits the entire parts of the electrodes 113 and 114 located below the outflow port 112a to be dipped in water. Thus, it is possible to surely use the electrodes 113 and 114 inside the casing 110 effectively.

Moreover, in this embodiment, the outflow port 112a located in the upper position is so located as to make contact with the upper surface of the casing 110, meaning that the highest part of the outflow port 112a is at the same level as the upper surface of the casing 110. This permits almost all of the air present inside the casing 110 to be discharged through the outflow port 112a. As a result, the level of the water that flows into the casing 110 can surely be raised to an upper portion of the casing 110. Thus, it is possible to more surely use the electrodes 113 and 114 inside the casing 110 effectively.

(3-2. Construction of the Shower Emitter)

Next, the shower emitter 200 will be described. As shown in FIGS. 7 and 8, the shower emitter 200 so operates that the water obtained via the ion elution unit 100 serving as an adder is sprayed in the form of a shower onto a target to be fed with water.

Here, water in the form of a shower denotes small water particles (liquid droplets) that are intermittently poured onto the target (here, laundry) put in the washing tub 30. The shower emitter 200 has a narrowed emission nozzle, and feeds in a predetermined period of time a predetermined amount of or more water mixed with air to the nozzle, so that such shower water is sprayed from the nozzle.

There is no particular restriction on the diameter (size) of the water particles of shower water. The smaller the water particles, the more they are like mist or spray, and thus he larger their surface areas as compared with the same amount of water. The larger the surface areas of the water particles, the larger the areas over which they make contact with air, and thus the more quickly they dry. The essence of the present invention lies in quickening as much as possible the drying of the water that is sprayed onto a target so as to be attached thereto with a view to making larger the crystals of the treatment substance dissolved in the water. Accordingly, if consideration is given only to the ease of drying, it is preferable to use shower water in the form of a mist.

However, since the pressure of tap water is fixed, the smaller the water particles of shower water is made by narrowing the nozzle, the longer the time required to feed (spray) a unit amount of water. Thus, the size of the water particles of the shower water (or the size of the nozzle orifice) should be determined appropriately with consideration given to the balance between the drying speed of water particles and the time required to feed water. Even shower water with comparatively large water particle size, such as that obtained from a shower apparatus installed in a bathroom, has a larger surface area as compared with the same amount of water, and is therefore easier to dry. Thus, even with such water, it is possible to satisfactorily achieve the effects of the present invention described later.

There are provided two of the shower emitter 200 for spraying shower water as described above so as to correspond to the plurality of outflow ports 112 described above. Specifically, for the outflow port 112a is provided a shower emitter 200a, and for the outflow port 112b is provided a shower emitter 200b. These shower emitters 200a and 200b are located above the washing tub 30 so as to spray water in the form of a shower toward the interior of the washing tub 30.

In this embodiment, the shower emitters 200a and 200b are respectively connected via the linking pipes 250a and 250b to the outflow ports 112a and 112b in such a way that the shower emitters 200a and 200b are located at different heights. Specifically, the shower emitter 200a is located in a position higher than the shower emitter 200b, with a height difference H of, for example, 1 cm.

This height difference between the shower emitters 200a and 200b produces a difference in the water pressure (a difference in the water head) between the shower emitter 200a located in a higher position and the shower emitter 200b located in a lower position when the feeding of metallic ion water to the target is being stopped (when no water is being fed in). Thus, when no water is being fed in, even if metallic ion water remains in the entire water feeding apparatus 300, the remaining water flows from the shower emitter 200a located in the higher position via the linking pipe 250a, ion elution unit 100, and linking pipe 250b to the shower emitter 200b located in the lower position, and is then discharged from the shower emitter 200b. Thus, when no water is being fed in, no metallic ion water remains inside the casing 110. This makes it possible to more surely prevent the above-mentioned inconveniences ascribable to the remaining water, such as short-circuiting between the electrodes 113 and 114 ascribable to the metallic ion contained in the remaining water and the destruction of the casing 110 resulting from the freezing of the remaining water.

Moreover, in this embodiment, the shower emitter 200b located in the lower position is located in a position lower than the lower ends A of the electrodes 113 and 114 of the ion elution unit 100. This permits the portion of the water remaining inside the ion elution unit 100 that is present above the shower emitter 200b located in the lower position to be discharged. Thus, the parts of the electrodes 113 and 114 inside the ion elution unit 100 located above the shower emitter 200b are never dipped in the remaining watery. This makes it possible to prevent short-circuiting between the electrodes 113 and 114 ascribable to the metallic ion contained in the remaining water.

(4. Configuration of the Drive Circuit)

Figure 10:
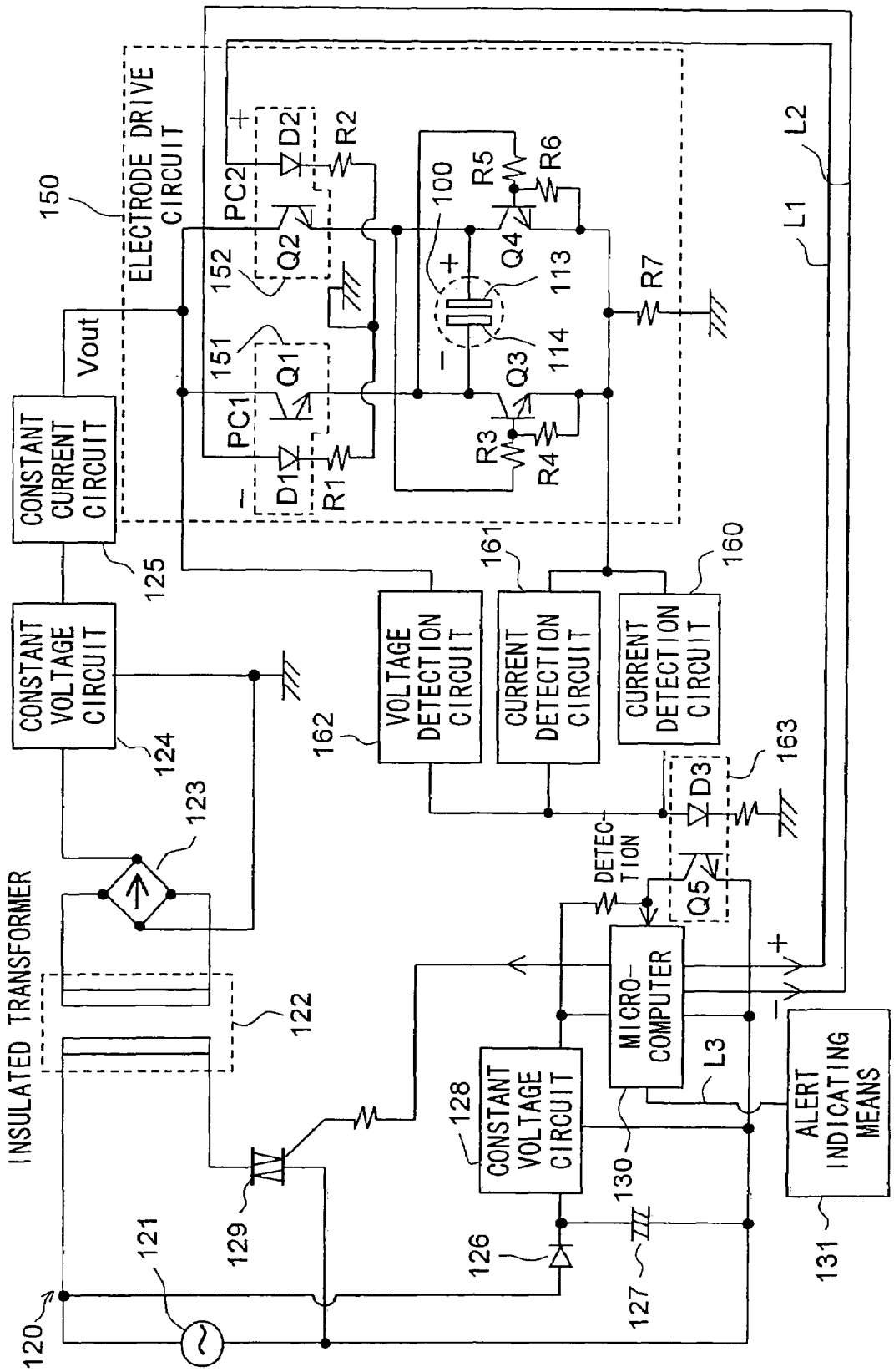
[FIG. 10] A diagram illustrating an outline of the configuration of the drive circuit of the above ion elution unit.

Next, with reference to FIG. 10, the control circuit 120 for driving the ion elution unit 100 will be described. FIG. 10 is a diagram illustrating an outline of the configuration of the control circuit 120.

Commercial electric power 121 is connected to a transformer 122, and this transformer 122 steps the 100 V voltage down to a predetermined voltage. The output voltage of the transformer 122 is rectified by a full-wave rectifier circuit 123, and is then regulated by a constant voltage circuit 124 into a constant voltage. The constant voltage circuit 124 is connected to a constant current circuit 125. The constant current circuit 125 operates so as to feed a fixed current to an electrode drive circuit 150, which will be described later, irrespective of the variation of the resistance across the electrode drive circuit 150.

The commercial electric power 121 is connected also, parallel to the transformer 122, to a rectifying diode 126. The output voltage of the rectifying diode 126 is smoothed by a capacitor 127, is then regulated into a constant voltage by a constant voltage circuit 128, and is then fed to a microcomputer 130. The microcomputer 130 controls the starting of a triac 129 that is connected between one end of the primary coil of the transformer 122 and the commercial electric power 121.

The electrode drive circuit 150 is composed of NPN-type transistors Q1 to Q4, diodes D1 and D2, and resistors R1 to R7, and these are interconnected together as shown in the figure. The transistor Q1 and the diode D1 together constitute a photocoupler 151, and the transistor Q2 and the diode D2 together constitute a photocoupler 152. That is, the diodes D1 and D2 are photodiodes, and the transistors Q1 and Q2 are phototransistors.

Now, suppose that the microcomputer 130 feeds a high-level voltage to a line L1 and a low-level voltage or an OFF voltage (zero voltage) to a line L2. Then, the diode D2 turns on, and correspondingly the transistor Q2 turns on. When the transistor Q2 turns on, a current flows through the resistors R3, R4, and R7, and thus a bias is fed to the base of the transistor Q3, turning this transistor Q3 on.

On the other hand, the diode D1 remains off, and accordingly the transistor Q1 is off, and the transistor Q4 also is off. In this state, a current flows from the positive-side electrode 113 to the negative-side electrode 114. As a result, inside the ion elution unit 100, a metallic ion as a positive ion is produced along with a negative ion.

When a current is passed through the ion elution unit 100 in one direction for a long time, while the electrode 113 on the positive side in FIG. 10 wears, the electrode 114 on the negative side collects, in the form of scale deposited firmly thereon, impurities such as calcium contained in water. Moreover, chlorides and sulfides of the metal of which the electrodes are made form on the surface thereof. These degrade the performance of the ion elution unit 100. To avoid this, in this embodiment, the electrode drive circuit 150 can be operated with the polarities of the electrodes reversed.

To reverse the polarities of the electrodes, the microcomputer 130 switches its control so as to reverse the voltages fed to the lines L1 and L2 so that a current flows between the electrodes 113 and 114 in the opposite direction. As a result of this switching, the transistors Q1 and Q4 are turned on, and the transistors Q2 and Q3 are turned off. The microcomputer 130 incorporates a counter function, and performs this switching every time a predetermined count is reached.

If, as a result of a variation in the resistance across the electrode drive circuit 150, in particular in the resistances of the electrodes 113 and 114, the current flowing between the electrodes decreases or a similar situation is encountered, the constant current circuit 125 raises the output voltage thereof to prevent a decrease in the current. However, as the accumulated use time increases, the ion elution unit 100 ultimately reaches the end of the useful life thereof. When this happens, it is no longer possible to prevent a decrease in the current even by reversing the polarities of the electrodes, or by switching to an electrode cleaning mode for forcibly removing the impurities deposited on the electrodes by keeping them at the particular polarities for a longer time than usual, or by raising the output voltage of the constant current circuit 125.

To cope with this, in the circuit under discussion, the current flowing between the electrodes 113 and 114 of the ion elution unit 100 is monitored by monitoring the voltage across the resistor R7, and, when this current becomes equal to the minimum permissible current level, it is detected by a current detecting means. A current detection circuit 160 serves as the current detecting means. The information that the minimum permissible current level has been detected is fed from a photodiode D3 included in a photocoupler 163 via a phototransistor Q5 included in the same photocoupler 163 to the microcomputer 130. The microcomputer 130 then drives, via a line L3, an indicating means to make it give out a predetermined warning indication. An alert indicating means 131 serves as the indicating means. The alert indicating means 131 is provided in the operation/display unit 81 or the control unit 80.

Moreover, to cope with a fault such as a short circuit within the electrode drive circuit 150, there is provided a current detecting means for detecting that the current has become higher than the maximum permissible current level. On the basis of the output of this current detecting means, the microcomputer 130 drives the alert indicating means 131. A current detection circuit 161 serves as the current detecting means. Likewise, when the output voltage of the constant current circuit 125 becomes lower than a predetermined minimum level, a voltage detection circuit 162 detects it, and the microcomputer 130 drives the alert indicating means 131. The microcomputer 130 may be provided separately as one dedicated for the operation of the electrode drive circuit 150, or may be integrated into the microcomputer provided in the control unit 80 for controlling the washer as a whole.

The control circuit 120 provided in the control unit 80 is configured as described above. Thus, the control unit 80 can control the application of a voltage to the electrodes 113 and 114 provided inside the ion elution unit 100, and thereby control whether or not to add the silver ion eluted from the electrodes 113 and 114 to the water inside the casing 110. Moreover, the control unit 80 can control the magnitude of the current fed between the electrodes 113 and 114 and the duration for which to apply the voltage thereto, and thereby control the amount of the metal ion eluted, i.e., the concentration of the metallic ion in metallic ion water.

This is convenient because it is possible to electrically perform all the necessary control and adjustments, such as whether or not to add a metallic ion and in what concentration to add it, which are impossible with a method whereby a metallic ion is eluted from a material such as zeolite containing a metallic ion. Furthermore, the control unit 80 can control the openness of the feed valve 50 (shower feed valve 50c) to control the amount of water (the floor rate, or flow speed of the water) fed to the ion elution unit 100 per unit time, and thereby control the metallic ion concentration in the metallic ion water.

Moreover, the control unit 80 can control the application of the voltage to the electrodes 113 and 114 and thereby control whether or not to add the eluted silver ion to water, and thus functions as a controlling means for controlling the addition of the silver ion to water in the adder (ion elution unit 100) so that either first water containing the silver ion as a treatment substance or second water containing no treatment substance is sprayed from the shower emitter 200 to the target (laundry).

Here, in a case where, in the washing tub 30 of the washer 1, different parts of the laundry put therein as a target to be fed with water lie on top of one another in many layers, when the first water is sprayed onto the laundry, the amount of the silver ion attached to the part of the laundry located at the surface thereof, where the first water directly hits the laundry, increases. In such a case, it is advisable to make the control unit 80 control in such a way that first the first water is sprayed onto the target and thereafter the second water is sprayed from the shower emitter 200 to the target. This control can be achieved in the following manner. First, while water is kept fed via the ion elution unit 100 to the shower emitter 200, the control unit 80 applies a voltage to the electrodes 113 and 114 of the ion elution unit 100 to elute the silver ion into water; then, while water is kept fed in the same manner, the application of the voltage is stopped so that the elution of the silver ion is stopped.

In this case, with the spraying of the second water, the silver ion attached to the superficial part of the laundry where the first water hits it can be moved into the interior part of the laundry. That is, it is possible to spread the silver ion all over the laundry. This makes it possible to obtain the antimicrobial effect of the silver ion uniformly all over the laundry.

Moreover, by making the control unit 80 spray first the first water (add the silver ion) and then the second water (stop the addition of the silver ion), even when water remains inside the ion elution unit 100 at the end of operation, the remaining water is the second water containing no silver ion. Thus, even when water remains inside the ion elution unit 100, it is possible to surely prevent the silver ion from precipitating as silver compounds and causing short-circuiting between the electrodes 113 and 114.

Reversely, the control unit 80 may so operate as to spray first the second water and thereafter the first water from the shower emitter 200. In this case, the spraying of the second water makes the laundry wet in advance, and thereafter spraying the first water containing the silver ion onto the surface of the laundry permits the silver ion to gradually penetrate deeper inside with the help of the water that has previously penetrated the laundry. Accordingly, even when different parts of the laundry lie on top of one another inside the washing tub 30, it is possible to obtain the antimicrobial effect of the silver ion over a wider area inside the laundry than in a case where only the first water is sprayed onto the laundry.

(5. Operations Performed in Antimicrobial Treatment Courses)

Next, the operation of the washer 1 provided with the ion elution unit 100 and the control unit 80 described above, as performed when an antimicrobial treatment course is selected as a washing course on the operation/display unit 81, will be described.

When an antimicrobial treatment course is selected, basically, while a desired standard course selected simultaneously on the operation/display unit 81 is being performed, under the control of the control unit 80, shower water containing the silver ion (first water) or shower water not containing the silver ion (second water) is sprayed from the shower emitter 200 with predetermined timing.

FIG. 11 shows the contents of standard and antimicrobial treatment courses. In the figure, (1) indicates the contents of a standard course, and (2) to (6) indicate the contents of antimicrobial treatment courses. In the figure, a circle "○" indicates that the corresponding process is included in the washing procedure, and a double circle "◎" indicates that, while the corresponding process is being performed, water is fed in in the form of a shower from the shower emitter 200.

Here, it is assumed that, in any of the courses, all types of processes for washing, namely, washing, rinsing, spin-drying, and drying, are performed. In practice, it is possible to omit any of these types of processes, or to perform only one particular type of process, for example by performing only washing, rinsing, and spin-drying with drying omitted, or by performing only rinsing.

Now, the different antimicrobial treatment courses will be described one by one.

(5-1. Antimicrobial Treatment with Silver Ion Shower (Rinsing 1 or 2))

When one of these antimicrobial treatment courses (the courses (2) and (3) in FIG. 11) is selected, during the rinsing process included in the washing procedure, the control unit 80 performs control such that the first water containing the silver ion is sprayed from the shower emitter 200.

As shown in the figure, in the rinsing process included in the washing procedure, shower rinsing or stored-water rinsing is performed. In shower rinsing, laundry is rinsed in the washing tub 30 while normal tap water is kept fed in (the main feedwater) in the form of a shower. On the other hand, in stored-water rinsing, water fed in from the water server unit 53 is stored in the washing tub 30, and laundry is rinsed in this water.

In such a rinsing process, by spraying the first water containing the silver ion from the shower emitter 200, as laundry is rinsed, the first water attaches to the laundry. This permits the silver ion contained in the first water to attach to the laundry, and thereby makes it possible to apply the antimicrobial effect of the silver ion to the laundry. That is, with the first water sprayed from the shower emitter 200, it is possible to treat the laundry with antimicrobial treatment.

Here, in the antimicrobial treatment course (2) in FIG. 11, the rinsing process may be performed in one of various patterns; for example, (a) the rinsing process may include at least one shower rinsing process but no stored-water rinsing at all, or (b) the rinsing process may include at least one shower rinsing process and a stored-water rinsing, with the shower rinsing process performed after the stored-water rinsing.

In a case where, as described just above, the last process performed in the rinsing process is at least one shower rinsing process, if the antimicrobial treatment course (2) mentioned above is selected, the control unit 80 performs control such that the first water containing the silver ion is sprayed from the shower emitter 200 in the last shower rinsing process. In a case where only one shower rinsing process is performed, this shower rinsing process is treated as the last shower rinsing process.

In a case where a plurality of shower rinsing processes are performed with the main feedwater, if the first water is sprayed in any of the shower rinsing processes other than the last, even when the silver ion contained in the first water attaches to the surface of laundry, the silver ion is thereafter washed off by the shower water (the main feedwater) fed in in the succeeding shower rinsing process. Thus, not only is it impossible to apply the antimicrobial effect of the silver ion to the laundry, but the silver ion is wasted.

However, by spraying the first water from the shower emitter 200 in the last shower rinsing process, it is possible to prevent the silver ion from being washed off as soon as it has attached to the surface of laundry. In this way, it is possible to reduce the amount of the silver ion that is wasted as compared with when the first water is sprayed in a shower rinsing process other than the last.

Here, the control unit 80 may perform control such that the second water not containing the silver ion is sprayed from the shower emitter 200 in any rinsing process other than the last shower rinsing process (including any shower rinsing process performed before it). In this case, the second water can be used as rinsing water for rinsing laundry that has gone through a washing process.

On the other hand, in the antimicrobial treatment course (3) in FIG. 11, i.e., when the rinsing process includes at least a stored-water rinsing process and in addition this stored-water rinsing process is the last rinsing process, the controlling means (control unit 80) performs control such that the first water is sprayed from the shower emitter 200 in the last stored-water rinsing process.

In this case, it is possible to adjust, according to the amount of the first water sprayed from the shower emitter 200, the amount of the silver ion contained in the rinsing water stored in the washing tub 30. That is, by adjusting the ratio of the amount of the first water sprayed and the amount of the main feedwater from the water server unit 53, it is possible to adjust the concentration of the silver ion in the rinsing water.

For example, suppose that the washer 1 is so designed that the current passed between the electrodes 113 and 114 of the ion elution unit 100 is 29 mA, that the flow rate of the water fed via the shower feed valve 50c is 2 L/min, and that the amount of water stored in the washing tub 30 for stored-water rinsing is 40 L. Then, if the silver ion concentration in the first water sprayed from the shower emitter 200 is assumed to be 900 ppb (parts par billion), feeding the first water in the form of a shower for two minutes, for example, results in feeding in 4 L of 900 ppb silver ion water. Thereafter, by feeding water (tap water) not containing the silver ion via the main feed valve 50a or the like, it is possible to dilute the silver ion concentration to one-tenth. Thus, in the washing tub 30, 40 L of 90 ppb silver ion water is obtained.

The silver ion concentration in the silver ion water in the washing tub 30 can be decreased to below 90 ppb by decreasing the amount of 900 ppb silver ion water sprayed, and can be increased to above 90 ppb by increasing the amount of 900 ppb silver ion water sprayed.

Alternatively, it is also possible to feed water in simultaneously via the main feed valve 50a and the shower feed valve 50c into the washing tub 30 and meanwhile apply a voltage to the electrodes 113 and 114 of the ion elution unit 100 for two minutes. The feeding of water via the two feed valves is continued until the total amount of water fed in reaches 40 L. Even in this case, an amount of silver equivalent to 4 L of 900 ppb silver ion water is eluted from the electrodes 113 and 114, and thus, when the total amount of water fed in reaches 40 L, 90 ppb silver ion water is obtained.

In this way, in the stored-water rinsing process, by making the control unit 80 spray the first water containing the silver ion from the shower emitter 200, it is possible to adjust the silver ion concentration in the rinsing water. Thus, it is possible to appropriately adjust the silver ion concentration in the rinsing water according to the bath ratio (the ratio of the amount of water to the amount of laundry). As a result, in the rinsing process, it is possible to perform the desired antimicrobial treatment that suits the given bath ratio.

Here, to study the effect of the silver ion concentration in silver ion water on germs, testing was conducted in which silver ion water was mixed with germ-infected fluid and the number of germs remaining after the lapse of a predetermined period of time was measured. Used as the germs was Cladosporium, a kind of black mold that often infects a washer to annoy the user. When the initial number of germs was set at $3 \times 10^5$/mL, the period of time required to reduce it to one-tenth was, with a silver ion concentration of 90 ppb, 24 hours and, with a silver ion concentration of 600 ppb, 3 hours. Thus, by increasing the silver ion concentration, it is possible to enhance the effect of the silver ion.

By using silver ion water of any of such sorts in a tub cleaning course, it is possible to prevent the proliferation of mold. Simply by using it for ordinary washing, it is possible to suppress mold proliferation. The higher the concentration, the more effective.

In a case where the washing tub 30 is a holeless tub, it is possible to provide, as a tub cleaning course, a course in which cleaning is performed with an amount of water that barely permits the pulsator 33 to be completely dipped in the water. Specifically, in a case where the washer 1 is provided with an input handler (operation/display unit 81) for permitting the setting of a washing course and an operation controller (control unit 80) for controlling the operation of the washing course set via the input handler, and in addition the washing tub 30 is a holeless tub, when a tub cleaning course is set as a washing course via the input handler, the operation controller may control the operation of the tub cleaning course in such a way that the tub is cleaned with an amount of water sufficient to permit the agitating member (pulsator 33) for agitating the laundry put in the holeless tub to be fully dipped in the water.

With a small amount of water, it is easy to increase the concentration of silver. Thus, in the construction descried above, it is easy to increase the effect on mold. Moreover, where the washing tub 30 is a holeless tub, the only part thereof where the collection and entry of mold is likely is around the pulsator 33. Thus, even with a small amount of water, it is possible to obtain a satisfactory effect. For example, by using about 6 L of 600 ppb silver ion water, it is possible to obtain a satisfactory effect on the mold that collects on the pulsator 33. Moreover, the amount of silver used is 3.6 mg, which is equivalent to using 40 L of 90 ppb silver ion water. This helps suppress the effect on the useful life of the silver electrodes.

Moreover, since the operation controller controls the operation of the tub cleaning course in such a way that the tub is cleaned with water containing a metallic ion (for example, the silver ion) as described above, it is possible, by exploiting the action of the metallic ion, to effectively suppress the proliferation of germs and mold inside the holeless tub and on the surface of the pulsator 33.

(5-2. Antimicrobial Treatment with Silver Ion Shower (Spin-Drying))

When this antimicrobial treatment course (the course (4) in FIG. 11) is selected, during the spin-drying process included in the washing procedure, the control unit 80 performs control such that the first water containing the silver ion is sprayed from the shower emitter 200.

Prior to the spin-drying process, the rinsing process described above is performed. In this rinsing process, laundry comes to contain ample water. Accordingly, spraying the first water containing the silver ion from the shower emitter 200 in the spin-drying process performed thereafter permits the first water to attach to the surface of the laundry, and also makes it easy for the silver ion contained in the attached first water to familiarize with and seep deep into the laundry. As a result, it is possible to apply the antimicrobial effect of the silver ion almost all over the laundry.

As another example of the spin-drying process, the control unit 80 may perform control such that, after spin-drying, the first water containing the silver ion is sprayed from the shower emitter 200. That is, here, the operations performed from the start of spin-drying up to the spraying of the first water after the spin-drying are as a whole called a spin-drying process. Laundry is somewhat dry even after spin-drying, and therefore shower-spraying the first water onto the laundry makes it easy for the silver ion contained in the first water to familiarize with and seep deep into the laundry. As a result, just as in the case described above, it is possible to apply the antimicrobial effect of the silver ion almost all over the laundry.

(5-3. Antimicrobial Treatment with Silver Ion Shower (Rinsing & Spin-Drying))

When this antimicrobial treatment course (the course (5) in FIG. 11) is selected, during both the rinsing and spin-drying processes included in the washing procedure, the control unit 80 performs control such that the first water containing the silver ion is sprayed from the shower emitter 200.

Under this control, the silver ion is attached to laundry in two processes, namely the rising and spin-drying processes. Thus, as compared with a case where the silver ion is attached to laundry in only one of those processes, it is possible to more surely attach the silver ion to laundry, and to attach a larger amount of the silver ion to laundry. As a result, it is possible to surely obtain a high antimicrobial effect due to the silver ion in laundry.

(5-4. Antimicrobial Treatment with Silver Ion Shower (Drying))

When this antimicrobial treatment course (the course (6) in FIG. 11) is selected, during the drying process included in the washing procedure, the control unit 80 performs control such that the first water containing the silver ion is sprayed from the shower emitter 200.

For example, even when laundry is dried not forcibly but spontaneously, crystals of the silver ion precipitate on the surface of the laundry. In this case, however, since drying proceeds slowly, crystals with large particles and few lattice defects form. These crystals have large surface areas and few lattice defects, and therefore make it more difficult for the silver ion to be eluted when it makes contact with moisture next time, resulting in the silver ion exerting a diminished antimicrobial effect in laundry.

However, when laundry is subjected to a drying process in which it is forcibly dried, for example, with warm air fed thereto, and in addition the first water containing the silver ion is sprayed from the shower emitter during that drying process, the first water first attaches to the laundry and then dries more quickly than when spontaneously dried. As a result, crystals with smaller particles and more lattice defects form. This makes it easier for the silver ion to be eluted when it makes contact with moisture next time, and thus makes it easier for the silver ion to exert the antimicrobial effect thereof in laundry.

During the above drying process, the control unit 80 may perform control such that the spraying of the first water from the water feeding apparatus 300 is performed and stopped alternately. In this case, during the period after the first water is sprayed one time and before it is sprayed next time, the first water that has previously sprayed onto the laundry dries. This permits the first water that has previously attached to the laundry to dry quickly on a little-by-littlie basis. As a result, crystals with still smaller particles and still more lattice defects form. This makes it still easier for the silver ion to be eluted, and thus makes it still easier for the silver ion to exert the antimicrobial effect thereof.

(5-5. Other Operations that can be Performed During an Antimicrobial Treatment Course)

In any of the antimicrobial treatment courses described above, the control unit 80 may perform control such that, while the first water containing the silver ion is being sprayed, the washing tub 30 is rotated. Rotating the washing tub 30 permits the laundry put therein to move. This prevents the first water being sprayed from being kept sprayed onto the same part on the surface of laundry, and thus helps alleviate uneven spraying of the first water onto laundry.

The control unit 80 may be so configured as to rotate the pulsator 33 (agitating member) for agitating laundry while the first water is being sprayed. When the pulsator 33 is rotated while the first water is being sprayed, laundry is agitated. Thus, even when different parts of the laundry lie on top of one another, it is possible to spray the first water all over the laundry. This permits the silver ion contained in the first water to spread uniformly all over the laundry, and thereby makes it possible to obtain the antimicrobial effect peculiar to the silver ion all over the laundry. Here, by making the control unit 80 rotate the pulsator 33 simultaneously as it makes the washing tub 30 rotate as described above, it is possible to attach the silver ion more uniformly to the laundry.

The control unit 80 may perform control such that, while the first water is being sprayed, air is sent to laundry. Air may be sent to laundry not only in the drying process but also in the rinsing or spin-drying process. By sending air to laundry while the first water is being sprayed, the first water attached to the laundry dries more quickly, and thus it is possible to securely produce crystals with smaller particles and more lattice defects. This makes it still easier for the silver ion contained in the first water to be eluted, and thus makes it still easier for the silver ion to exert the antimicrobial effect thereof.

The control unit 80 may perform control such that the first water containing the silver ion is sprayed from the water feeding apparatus 300 by combining together two or more of the antimicrobial treatment courses (2) to (6) described above. Specifically, the control unit 80 may perform the shower-spraying of the first water containing the silver ion from the shower emitter 200 in two or more of the rinsing, spin-drying, and drying processes included in the washing procedure. In the antimicrobial treatment course (5) described above, the first water is shower-sprayed in two processes, namely the rinsing and spin-drying processes, included in the washing procedure. Likewise, by shower-spraying the first water in a plurality of processes included in the washing procedure, it is possible to increase the amount of the silver ion attached to laundry, and thereby obtain the antimicrobial effect of the silver ion to the full.

On the basis of the foregoing, it can be concluded that the control unit 80 has to perform control such that the first water is sprayed from the shower emitter 200 during at least one of a rinsing process, a spin-drying process, and a drying process.

In which process to shower-spray the first water containing the silver ion may be determined by the control unit 80 according to the type of laundry or according to the contents of the standard course selected on the basis of the type of laundry. The control unit 80 may then, according to the determination thereof, shower-spray the first water from the shower emitter 200.

For example, when an antimicrobial treatment course is set in combination with, as a standard course, the soft course, the control unit 80 may so control that the antimicrobial treatment course (3) is performed. That is, in this case, the control unit 80 performs the shower-spraying of the first water only during the rinsing process (in particular, stored-water rinsing) included in the washing procedure. On the other hand, when an antimicrobial treatment course is set in combination with, as a standard course, the dry course, the control unit 80 may so control that the antimicrobial treatment course (5) is performed. That is, in this case, the control unit 80 performs the shower-spraying of the first water during the rinsing and spin-drying processes included in the washing procedure.

Under such control by the control unit 80, it is possible to attach the silver ion to laundry appropriately according to the type of the laundry. Thus, with any type of laundry, it is possible to apply thereto the antimicrobial effect of the silver ion.

The timing with which the first water containing the silver ion is shower-sprayed may be selected or specified according to the settings made by the user on the operation/display unit 81. For example, by default, the timing of shower-spraying is set to be during the stored-rinsing process, and, when thorough antimicrobial treatment is desired, the user can, on the operation/display unit 81, change the timing to both the stored-rinsing and spin-drying processes.

(6. Amount of Silver Attached)

Next, a preferred range of the amount of silver attached to the surface of laundry by the shower-spraying of the first water containing the silver ion will be described.

With respect to this embodiment, testing was conducted to study the relationship among the amount of silver attached per kilogram of laundry when the first water is shower-sprayed thereto, the antimicrobial effect exerted in the laundry when that amount of silver is attached thereto, and the smells given off from the laundry. The ultimate purpose is to find the preferred range of the amount of silver attached.

Here, the antimicrobial effect was evaluated by referring to the quantitative testing method (germ-infected fluid absorption method) based on JIS (Japanese Industrial Standard) L1902:2002. More specifically, a sheet of cloth A1 that has been desized but not treated with antimicrobial treatment and a sheet of cloth A2 that has been treated with antimicrobial treatment were each inoculated with germ-infected fluid, and these were left at a temperature of 37° C. for 18 hours. Then, the number of germs was measured on each sheet of cloth, and the difference between the two sheets in the increase or decrease of the number of germs as logarithmically calculated was found as the bacteriostatic activity value, on the basis of which the antimicrobial effect was evaluated. Testing using the quantitative testing method mentioned above is typically conducted by using *Staphylococcus aureus*. In this embodiment, however, *Trichophyton* was used instead.

For example, suppose that the numbers of germs after the lapse of 18 hours are $1.9 \times 10^7$/ml on the cloth A1 and $2.4 \times 10^6$/ml on the cloth A2, the bacteriostatic activity value equals $\log(1.9 \times 10^7) - \log(2.4 \times 10^6) = 0.9$. Table 1 shows the relationship between the silver ion concentration and the bacteriostatic activity value under these conditions.

TABLE 1

| Amount of Silver Attached (mg/kg) | 0 | 0.7 | 1 |
|---|---|---|---|
| Bacteriostatic Activity Value | 0.1 | 1 | 3.1 |

The results shown in Table 1 show that, as the amount of silver attached per kilogram of laundry monotonically increases, the bacteriostatic activity value monotonically increases. It is generally recognized that an antimicrobial effect can be obtained with a bacteriostatic activity value of 2 or more. Accordingly, as shown in Table 1, when the amount of silver attached per kilogram of laundry is 1 mg or more, the bacteriostatic activity value is 3.1 or more, and thus it is possible to obtain an antimicrobial effect.

Figure 12:
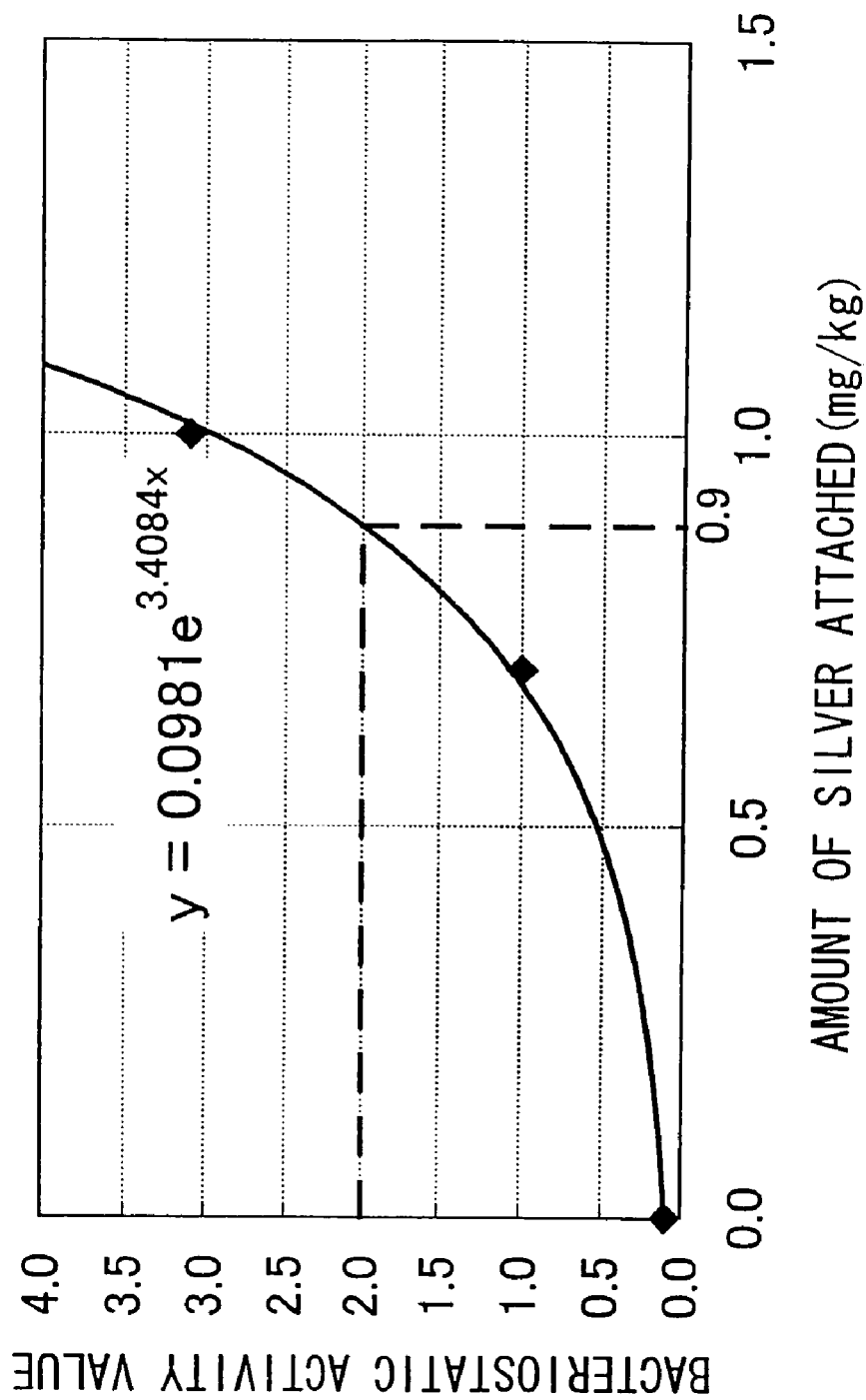
[FIG. 12] A graph showing the relationship between the amount of silver attached per kilogram of laundry and the bacteriostatic activity value.

To further study the relationship between the amount of silver attached and the bacteriostatic activity value, the results shown in Table 1 were tentatively plotted on a graph. FIG. 12 is a graphic representation of the relationship between the amount of silver attached and the bacteriostatic activity value based on the results shown in Table 1.

As shown in FIG. 12, it has been found that, when the amount of silver attached per kilogram of laundry is taken along the horizontal axis (x-axis) and the bacteriostatic activity value is taken along the vertical axis (y-axis), the curve that smoothly connects the three points of which the x and y coordinates are equal to the amount of silver attached and the bacteriostatic activity value shown in Table 1 can be approximated by a monotonically increasing function $y=0.0981 \exp(3.4084x)$. On the basis of this function, the amount of silver attached that yields a bacteriostatic activity value of 2, i.e., the value of x when y=2, is found to be x=0.88 (about 0.9).

Since it is recognized that an antimicrobial effect can be obtained with a bacteriostatic activity value of 2 or more, FIG. 12 shows that, when the amount of silver attached per kilogram of laundry is 0.9 mg or more, it is possible to obtain an antimicrobial effect.

The relationship between the amount of silver attached per kilogram of laundry and the light reflectivity obtained with that amount of silver attached also was studied. The results are shown in Table 2. Here, light reflectivity is given as a ratio relative to unity light reflectivity, namely 1, obtained when no treatment is performed (i.e., when the amount of silver attached is 0 mg/kg).

TABLE 2

| Amount of Silver Attached (mg/kg) | 0 | 10 | 19 |
|---|---|---|---|
| Reflectivity (Treated-to-Untreated Ratio) | 1 | 0.99 | 0.97 |

As the results shown in Table 2 indicate, when the amount of silver attached per kilogram of laundry was about 10 mg, the difference in light reflectivity as compared to when no treatment was performed was about 1%, and was not visually recognized. By contrast, when the amount of silver attached was 19 mg or more, the difference in light reflectivity as compared to when no treatment was performed was as large as 3%, and was visually recognized. This is considered to be because black substances originating from silver compounds had attached to the laundry. In white laundry, when such black substances attach thereto, they tend to be visible. Even in laundry that is not white, as washing is repeated, black substances may gradually become visible. Out of these considerations, it is believed that a preferred amount of silver attached per kilogram of laundry is less than 19 mg, and more preferably 10 mg or less.

Next, the relationship between the amount of silver attached per kilogram of laundry and the odors was studied. Sheets of cloth that have gone through a washing procedure (including spin-drying) were left, in a wet state, at 37° C. in an air-tight, constant-temperature bath for 18 hours. While sheets of cloth to which silver was not attached gave off foul odors, those to which 0.1 mg of silver was attached per kilogram of laundry did not under the same conditions. This suggests that, when the amount of silver attached per kilogram of laundry is 0.1 mg or more, it is possible to surely suppress, with the antimicrobial effect of the silver (silver ion) attached to the laundry, odors that are so strong that humans feel them to be foul.

When the relationship among the antimicrobial effect, the light reflectivity, and the odors is considered comprehensively, it is believed that the amount of silver to be attached per kilogram of laundry is 0.1 mg at the minimum, preferably 0.9 mg or more, and ideally 1 mg or more. On the other hand the upper limit of the amount of silver attached per kilogram of laundry is preferably less than 19 mg, and ideally 10 mg or less. Thus, a preferred range of the amount of silver attached per kilogram of laundry can be determined as one of different combinations of these lower and upper limits.

Figure 13:
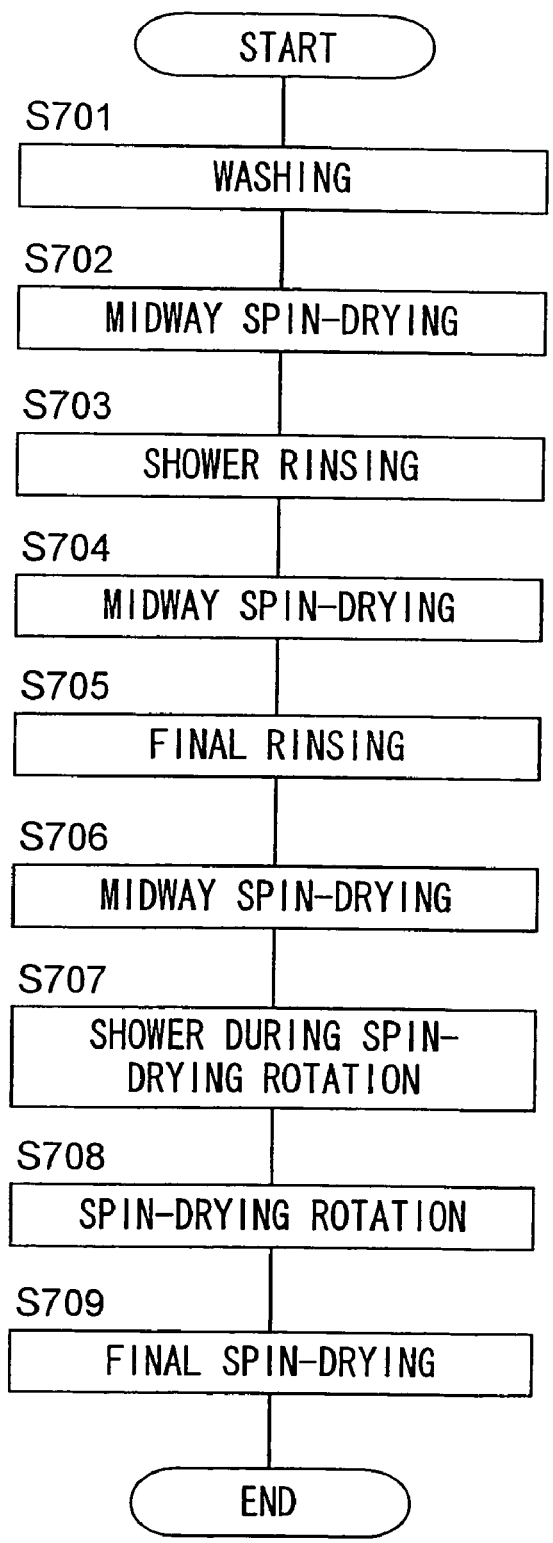
[FIG. 13] A flow chart showing an example of an operation sequence of the above washer.

Next, as one example, the amount of silver attached to laundry and the antimicrobial effect obtained when washing is performed through a sequence of operations as shown in FIG. 13 will be described. In this sequence, washing (S701), midway spin-drying (S702), shower rinsing (S703), and midway spin-drying (S704) were performed as in an ordinary sequence, and then, as final rinsing, stored-water rinsing was performed with 300 ppb silver ion water fed in (S705). Thereafter, midway spin-drying (S706) was performed, and meanwhile, while spin-drying rotation is performed at 100 rpm, a shower of 600 ppb silver ion water is sprayed for one minute (S707). Thereafter, the shower is stopped, but the spin-drying rotation is maintained for five minutes (S708). Thereafter, final spin-drying is performed (S709).

Here, in step S708, the washing tub 30 is rotated with the drain valve 68 closed, and this differs from what is performed in step S709, where the washing tub 30 is rotated with the drain valve 68 open. That is, in the sequence shown in FIG. 13, the control unit 80 (controlling means) controls the drain valve 68 for draining the water inside the washing tub 30 in such a way that draining is suspended for a predetermined period of time (in the above example, five minutes) after the end of the spraying of shower water from the shower emitter 200, and also controls the washing tub 30 so that it rotates during that predetermined period of time.

The above control of the drain valve 68 by the control unit 80 is achieved, for example, in the following manner. While a shower is still being sprayed from the shower emitter 200, the drain valve 68 is closed, and draining is suspended for a predetermined period of time (for example, five minutes) after the end of the spraying of the shower. Alternatively, after the end of the spraying of a shower from the shower emitter 200, the drain valve 68 is kept closed for a predetermined period of time (for example, five minutes) so that draining is suspended during this period.

Figure 14:
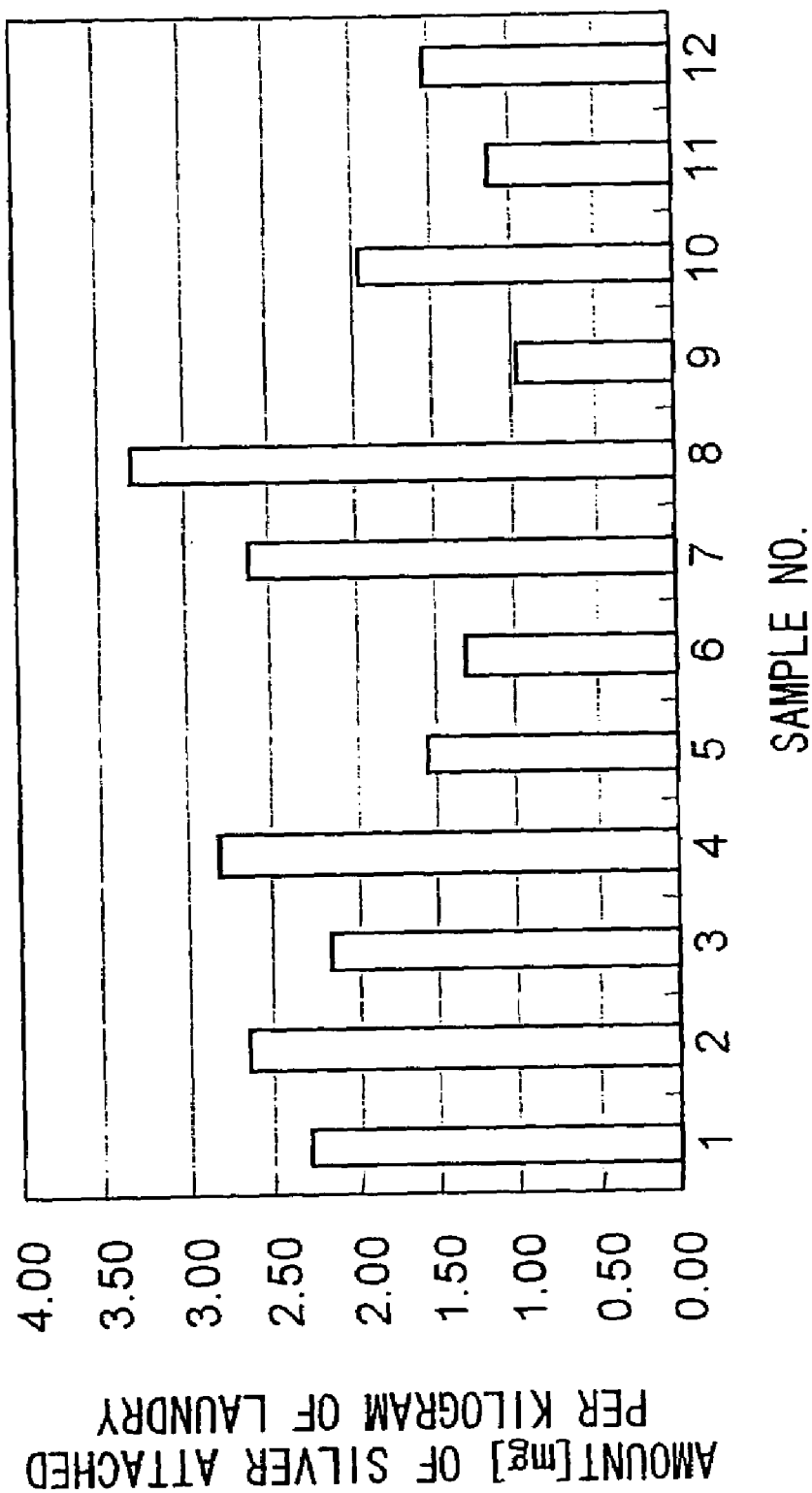
[FIG. 14] A graph showing the amount of silver attached to different samples when the washer was operated with the above operation sequence.

From among sheets of cloth washed through the sequence described above, 12 samples were extracted, and the amount of silver attached was measured on them. The results are shown in FIG. 14. As shown in this figure, in all the samples, the amount of silver attached per kilogram of laundry was 0.9 mg or more, the average being 2.0 mg. Then, samples produced under these conditions were subjected to testing conducted, by using *Trichophyton*, by referring to the quantitative testing method (germ-infected fluid absorption method) based on JIS (Japanese Industrial Standard) L1902:2002. In this testing, a bacteriostatic activity value of 2.0 or more was obtained, and thus an antimicrobial effect was obtained.

Moreover, samples produced through the sequence shown in FIG. 13 and samples that were subjected to stored-water rinsing using 90 ppb silver ion water as final rinsing without the spraying of a shower were subjected, by using *Pseudomonas aeruginosa* as germs, to the quantitative testing method (germ-infected fluid absorption method) based on JIS (Japanese Industrial Standard) L1902:2002. Whereas the former yielded a bacteriostatic activity value of 2.0 or more, and thus yielded an antimicrobial effect, the latter yielded a bacteriostatic activity value of 2.0 or less.

Furthermore, with samples made of not cotton but polyester, which is a hydrophobic fiber, those produced through the sequence shown in FIG. 13 and those that were subjected to stored-water rinsing using 90 ppb silver ion water as final rinsing without the spraying of a shower were subjected, by using *Staphylococcus aureus* as germs, to the quantitative testing method (germ-infected fluid absorption method) based on JIS (Japanese Industrial Standard) L1902:2002. Whereas the former yielded a bacteriostatic activity value of 2.0 or more, and thus yielded an antimicrobial effect, the latter yielded a bacteriostatic activity value of 2.0 or less.

For comparison, when final spin-drying was performed immediately, without performing spin-drying rotation for five minutes, after the end of the spraying of a shower, the amount of silver attached per kilogram of laundry was 1.6 mg on average. This is considered to be because the silver ion sprayed in the form of a shower onto cloth takes time to seep into the texture, and thus, when final rinsing is performed immediately, the amount of silver attached diminishes. Accordingly, it can be said that, by making the control unit 80 keep the drain valve 68 closed for a predetermined period of time after the spraying of a shower, it is possible to permit the silver ion contained in the remaining water to seep deep into and be absorbed by the texture (i.e., not only the superficial part but also the interior part thereof).

Moreover, by performing spin-drying rotation (S708) during the predetermined period of time mentioned above, it is possible to permit the silver ion water fed in to move upward under centrifugal force and thereby permit the laundry that has moved outward inside the washing tub 30 during the previously performed midway spin-drying (S706) to make contact with water.

Figure 15A:
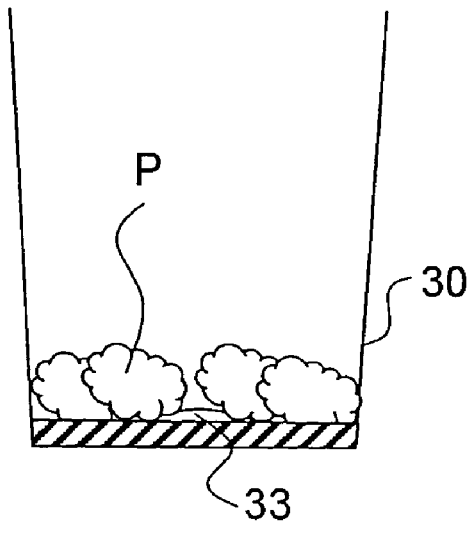
[FIG. 15] (a) A sectional view of the washing tub, with sprayed water collected at the bottom; (b) A sectional view of the washing tub, with the water inside it raised upward as a result of the rotation of the tub; (c) A sectional view of the washing tub, with laundry driven to the corner under centrifugal force as the washing tub rotates.

Specifically, by suspending draining for a predetermined period of time after the spraying of a shower, it is possible to permit the treatment substance to be absorbed by laundry (cloth). However, if the washing tub 30 remains at rest, as shown in FIG. 15A, the water containing the treatment substance sprayed in the form of a shower collects in a bottom portion of the washing tub 30 under gravity. In the bottom portion of the washing tub 30 is provided the pulsator 33, and thus, even when the drain valve 68 is closed, the water (indicated by hatching in the figure) collects under the pulsator 33, and thus does not make contact with the cloth P.

Figure 15B:
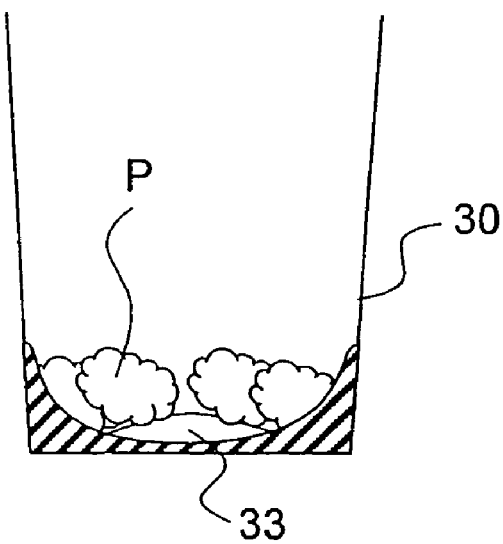
Figure 15C:
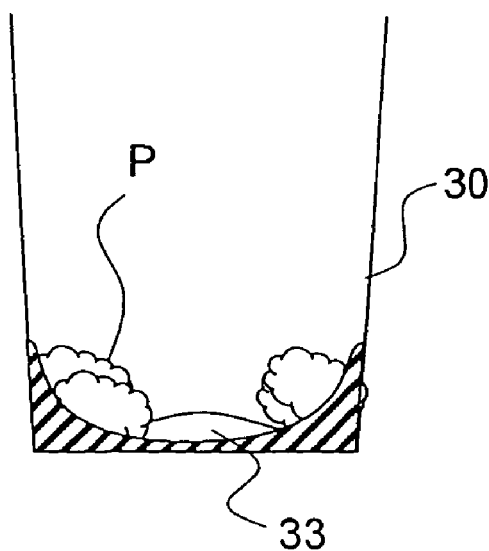

By contrast, when the washing tub 30 is rotated, the centrifugal force resulting from the rotation permits the water to rise as shown in FIG. 15B. This makes it possible to permit the water to make contact with the cloth P and thereby increase the amount of the treatment substance that attaches to the cloth P. In a case where midway spin-drying is performed before a process involving the spraying of shower water, as shown in FIG. 15C, the cloth P is driven to the corner under centrifugal force. Thus, a greater effect is obtained. When the washing tub 30 has no holes at least in a bottom portion thereof, the water containing the treatment substance does not flow out of the washing tub 30 through holes. Thus, a greater effect is obtained.

In the sequence shown in FIG. 13, the control unit 80 performs control such that the washing tub 30 is rotated while the drain valve 68 is closed. When the washing tub 30 is rotated, the water inside the washing tub 30 rises under centrifugal force as described above, and thus the water is not drained through the drain valve 68 located below. Accordingly, when the washing tub 30 is rotated after the spraying of a shower, the drain valve 68 does not necessarily have to be closed.

(7. Effects of the Present Invention)

As described above, a water feeding apparatus 300 according to the present invention is an apparatus (method) for feeding water to a target (for example, laundry) to be fed with water, and is provided with an adder (an ion elution unit 100) for adding a treatment substance (for example, the silver ion) to the water and a shower emitter 200 for spraying, in the form of a shower, the water fed thereto via the adder onto the target. Moreover, a method for feeding water according to the present invention uses a water feeding apparatus 300 according to the present invention to spray shower water to a target to be fed with water. As a result, the following effects can be obtained.

In a water solution, silver is present in the form of the silver ion ($Ag^+$). This silver ion exerts a disinfecting effect. As water containing the silver ion evaporates, the silver ion concentration in the water increases, with the result that the silver ion forms salts with negative ions present in the water, and precipitates as solid substances (silver compounds). As salts, AgCl, AgOH, and other compounds are supposed to be present. Since these are unstable, they decompose into $Ag_2O$ and Ag. Generally, $Ag_2O$ and Ag are nearly insoluble, but, in reality, the silver ion is eluted from $Ag_2O$ and Ag present at the surface of laundry, and exerts a disinfecting effect. It is known that the surface of a solid is unstable in terms of energy, and differs from the interior in properties and composition, with the result that elution and the like of the ingredients is more likely to take place at the surface. In the present invention, the silver ion is supposed to be eluted from the surface or the like of $Ag_2O$ and Ag.

When water containing the silver ion is dried, the silver ion precipitates in the form of a fine power (crystals) of silver compounds such as metal silver and silver oxide. When these substances make contact with water next time, the silver ion is eluted from the surface of their crystals, exerting a disinfecting effect.

By shower-spraying silver ion water (the first water) from the shower emitter 200 as in this invention, it is possible to increase the surface areas of liquid droplets of the silver ion water and thereby quicken the drying thereof. As silver ion water dries, the substances such as the silver ion dissolved therein precipitate as crystals. Here, the quicker the drying, the shorter the time in which the precipitation of crystals takes place, and thus the smaller the crystals obtained, and the more detects they include. Since the dissolution of crystals occurs at lattice defects including the surfaces of the crystals, the smaller the particles of crystals, and the more lattice defects they have, the more easily they dissolve. The silver ion is eluted from such crystals more easily, and this makes them effective in obtaining a disinfecting effect.

That is, according to the present invention, liquid droplets that have small particles and are thus easy to dry are shower-sprayed so as to be attached to the surface of laundry. This makes it easy for the silver ion contained in the liquid droplets to be eluted at the surface of laundry, and thus makes it easy for the silver ion to exert the antimicrobial effect peculiar thereto.

Accordingly, when silver ion water is shower-sprayed, by quickening the drying thereof, for example, by sending air thereto, it is possible to produce crystals with still more lattice defects so as to make it still easier for the silver ion to be eluted. In this way, it is possible to further enhance the antimicrobial effect of the silver ion.

Incidentally, the silver ion is not eluted from crystals of silver compounds in the complete absence of moisture. This, however, produces no problem since, in an environment completely free from moisture, germs perish.

In a case where laundry is water-repellent cloth, even when the laundry is dipped in silver ion water, almost no water remains in the cloth. This makes it impossible to effectively attach the silver contained in the silver ion water to the cloth. Even in a case where the laundry is not so far as water-repellent but hydrophobic cloth such as chemical fiber, it does not absorb much water, and therefore, even when it is dipped in silver ion water, not much water remains in the cloth, and thus not much silver remains in the cloth.

By contrast, in a case where liquid droplets of silver ion water are shower-sprayed so as to be attached to cloth as in the present invention, even if the liquid droplets do not seep into the cloth, by leaving them on the surface of the cloth to dry, it is possible to surely attach the silver contained in the liquid droplets to the cloth. Thus, it is possible to efficiently attach silver even to low-water-absorption cloth. Moreover, when silver is attached in this way, the amount of silver attached is little influenced by the cloth. Thus, even when the concentration of silver ion water is increased, it never occurs that too much silver is attached to high-water-absorption cloth.

Moreover, by spraying silver ion water in the form of a shower, it is possible to spread the silver ion all over the cloth with a small amount of water. This makes it possible to produce high-concentration silver ion water with the same amount of water, and thus to perform antimicrobial treatment with a high antimicrobial effect. Moreover, in this case, it is possible to save water.

Even with low-water-absorption cloth that does not absorb much water, since the silver ion in the form of a shower is attached directly thereto, it is possible to let much silver remain on the cloth. Moreover, by using a drying function, it is possible to reduce the time required for the silver ion water to dry and for the silver ion to stably attach to the cloth. This makes it possible to more efficiently let the silver ion remain on the cloth.

Even if the amount of silver attached is insufficient with a single session of treatment, by repeating the shower-spraying of silver ion water, it is possible to increase the amount of silver attached. For example, in silver ion rinsing in which antimicrobial treatment is performed with silver ion water stored in the water tub 30, laundry is completely dipped in water. Repeating such antimicrobial treatment causes the silver previously attached to the laundry to be washed off when dipped in water. Thus, repeated treatment proves to be not very effective. It is believed that, by using in each session of antimicrobial treatment silver ion water of the same concentration or of gradually increasing concentrations, it is possible to prevent the lowering of the antimicrobial effect resulting from the previously attached silver being washed off.

However, in a case where silver ion water is sprayed in the form of a shower as in this embodiment, since silver ion water is sprayed directly onto cloth, the previously attached silver is not washed off. On the contrary, it is possible even to attach an extra amount of silver. This makes repeated treatment involving repeated shower-spraying of silver ion water very effective.

In particular, if, after shower-spraying, the cloth is dried without being subjected to spin-drying, the silver ion is not washed off by the water drained during spin-drying. Thus, it is possible to stably attach the silver ion to cloth during drying. That is, in this case, it is possible to let all the silver ion remain on the cloth, and thereby to obtain a high antimicrobial effect exerted by the silver ion.

Moreover, by spraying silver ion water in the form of a shower, it is possible to spread the silver ion over a wide area on laundry (cloth) with a small amount of water. Accordingly, as compared with a method whereby laundry is dipped in silver ion water, it is possible to use higher-concentration silver ion water with the same amount of the silver ion. In general, to increase the amount of the silver ion eluted per unit time, it is necessary, for example, to increase the current that is passed between the electrodes 113 and 114. By contrast, according to the present invention, it is possible, without taking such measures, to permit an amount of silver as large as of the order of 1 mg to be attached per kilogram of laundry. On the other hand, an amount of silver comparable to that attached by the dipping method can be attached with reduced amounts of water and of silver used.

The water feeding apparatus 300 according to the present invention described above can be used also as a water spraying apparatus (for example, a dish washer-dryer). That is, it is possible to realize a water spraying apparatus that is provided with the water feeding apparatus 300 according to the present invention described above and that is so constructed that shower water is sprayed from the water feeding apparatus 300 onto a target to be fed with water.

In this way, by constructing a water spraying apparatus by using the water feeding apparatus 300 according to the present invention so that a target to be supplied with water is sprayed with shower water containing a treatment substance that suits the target, it is possible to quicken the drying of liquid droplets attached to the surface of the target so that the treatment substance crystallizes in a state that permits it to be easily eluted when it meets water next time. This makes it easier for the treatment substance to be eluted when it makes contact with moisture next time, and makes it easier for the treatment substance to exert the effect peculiar thereto that suits the target. In this way, it is possible to surely obtain different effects that suit different targets.

(8. Other Features)

Next, other features of the present invention will be described.

(8-1. Ion Elution Unit)

The construction of the ion elution unit 100 is as shown in FIGS. 7 to 9. In this ion elution unit 100, the electrodes 113 and 114 described above may be formed as electrodes that correspond to a plurality of metals.

As described earlier, the silver and zinc ions as metallic ions exert an excellent antimicrobial effect, and the copper ion exerts an excellent antifungal effect. Accordingly, when the electrodes 113 and 114 of the ion elution unit 100 are formed as electrodes corresponding to the silver (or zinc) ion or the copper ion, i.e., formed as silver (or zinc) electrodes or copper electrodes, it is possible to elute selectively either the silver (or zinc) ion or the copper ion or both. This makes it possible to obtain selectively either the effect of the silver (or zinc) ion or the effect of the copper ion or simultaneously both, leading to increased usefulness.

The electrodes 113 and 114, to which a positive and a negative voltage are applied respectively, of the ion elution unit 100 may be a pair of electrodes of which one is a silver electrode and the other is a copper electrode. Alternatively, the ion elution unit may be so constructed as to include a pair of electrodes of which both are silver electrode and another pair of electrodes of which both are copper electrodes.

In the former case described above, either by keeping the polarities of the voltages applied to the electrodes 113 and 114 constant or by reversing them at predetermined time intervals, it is possible to elute selectively both of the metallic ions. On the other hand, in the latter case described above, by applying voltages to both pairs of electrodes 113 and 114, it is possible to obtain both of the metallic ions, and, by applying voltages to only one of the two pairs of electrodes 113 and 114, it is possible to elute selectively only one of the two metallic ions.

The ion elution unit for eluting a metallic ion is not limited to the ion elution unit 100 specifically described above. The ion elution unit may be, for example, of the type that has an ion eluting material (for example, silver sulfide as a silver eluting material) housed in a cartridge and that elutes a metallic ion when water is passed through the cartridge (i.e., without application of a voltage). In this case, the control unit 80 can control the amount of the metallic ion contained in the shower-sprayed water by adjusting, with the shower feed valve 50c, the amount of water fed to the ion elution unit.

In this embodiment, only one ion elution unit 100 is provided so as to correspond to the shower feed valve 50c. It is, however also possible to provide two ion elution units 100 to correspond to the main feed valve 50a and the shower feed valve 50c, respectively. In this case, silver ion water can be fed as main feedwater into the washing tub 30 in a short time, and thus it is possible to perform antimicrobial treatment quickly in stored-water rinsing.

(8-2. Shower Emitter)

Figure 16:
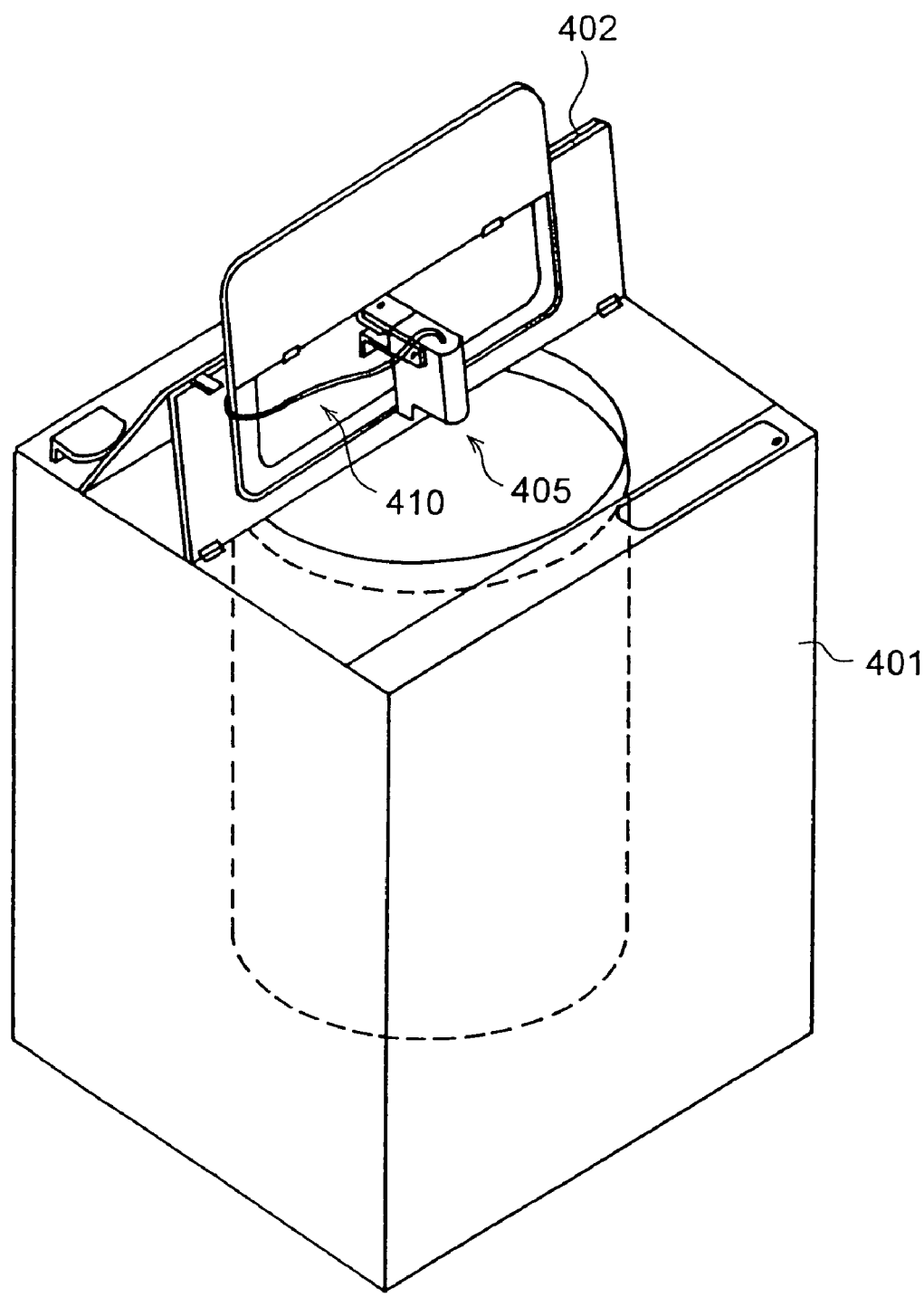
[FIG. 16] A perspective view showing an outline of the construction of another washer embodying the invention, with a supersonic vibrator used as the shower emitter.

The shower emitter 200 described in this embodiment has simply to spread moisture in the form of a shower all over the target to be fed with water, and thus may be of the type that emits a shower with a smaller amount of water, for example in the form of a mist or a spray. The shower emitter 200 may be not of the type that emits water in a plurality of directions when a shower is sprayed but of the type that spreads water by some means after emitting water. Even in a case where a nozzle that emits water only in one direction is used as the shower emitter 200, one of the nozzle and the target may be moved relative to the other so that the water is spread sufficiently over the surface of the target. Alternatively, a stream of air may be produced by the use of a fan or the like so that, on the principle of a Venturi tube, liquid is sucked up and formed into a mist to produce a shower. Alternatively, liquid may be acted upon by acceleration so as to be formed into liquid droplets, as by producing a mist by the use of a supersonic vibrator or the like FIG. 16 is a perspective view showing an outline of the construction of a washer 401 incorporating a shower emitter 200 employing a supersonic vibrator. On the top face of the washer 401 is provided an openable lid 402 through which to permit laundry to be put in and taken out of a washing tub. The lid 402 is fitted with a supersonic partial washing apparatus 405 (vibrator). Moreover, an unillustrated silver ion elution unit (corresponding to the ion elution unit 100) is provided in the route of a feed pipe 410 leading to the partial washing apparatus 405. Here, water is fed in in such a way that the water makes contact with a metal horn connected to the supersonic vibrator provided inside the partial washing apparatus 405.

The silver ion is eluted from the silver ion unit so that silver ion water is fed to the partial washing apparatus 405, and the horn is made to vibrate, with the result that the silver ion water is formed into a mist. When, by using this construction, silver ion water is attached to a target to be fed with water, an antimicrobial effect was obtained that was similar to that obtained in the washer 1 shown in FIG. 7, i.e., a construction where the silver ion is attached to the target by using a shower.

When a shower nozzle is used, to make the obtained liquid droplets small, the holes (emission orifices) need to be made small. However, small holes are liable to cause water to remain in the water feed route. Moreover, precipitates may cause clogging, or cause water to remain inside the ion elution unit. In particular, in a construction where the elution unit is provided with electrodes, precipitates may cause short-circuiting between the electrodes. To avoid this, it is necessary to secure easy drainage, as by providing a plurality of outflow ports. Moreover, when high-concentration silver ion water is used, or a high-viscosity treatment substance such as a softening agent is used, the holes themselves may be clogged.

By contrast, when a mist is produced by the use of a vibrator, it is possible to produce fine liquid droplets without making the holes smaller. This helps avoid the disadvantages mentioned above. Moreover, when the input of a signal to the vibrator is stopped, silver ion water can be fed without being formed into a mist. This is convenient when silver ion water is collected in a container so as to be used for other purposes.

Moreover, the washer 401 of this embodiment is of the type that is provided with a metal horn to which water is fed as necessary. However, the washer 401 may be so constructed that, instead of water being fed in as necessary, the horn or the vibrator is dipped in stored water.

Alternatively, a fan, air pump, or the like may be used to send or suck air so that a mist containing the silver ion is fed to the target. This makes it possible to exert an antimicrobial or other effect on a target extending in a wide area or located at a remote place.

The shower emitter does not necessarily have to be mounted on a washer, nor does the target of shower-spraying necessarily have to be laundry. Specifically, it is possible to spray a shower containing an antimicrobial ion such as the silver, copper, or zinc ion onto, for example, a kitchen sink, chopping board, toy, floor, carpet, bathtub, toilet, or urinal to obtain an antimicrobial effect. It is also possible to spray, in the form of a shower or the like, liquid droplets containing an antimicrobial ion into the air to remove germs present in the air. It is also possible to spray them onto a pet or plant to prevent odors and diseases ascribable to bacteria.

By spraying liquid droplets containing an antimicrobial ion onto food, it is possible to prevent the rotting of the food and keep the food fresh. As well as the silver, copper, and zinc ions, the nickel, palladium, platinum, rhodium, ruthenium, and other ions have an effect of retarding the aging and deterioration in freshness of plants caused by ethylene. Thus, by spraying liquid droplets containing such an ion on vegetables, fruits, and cut flowers, it is possible to keep them fresh.

(8-3. Treatment Substances)

In this embodiment, used as an example of the treatment substance that is added to the water that is fed to the adder (ion elution unit 100) is the silver ion. However, the treatment substance actually used is not limited to the silver ion. Another example of the treatment substance is a softening agent. A softening agent is added to water in the adder, and the water is sprayed in the form of a shower from the shower emitter 200 so as to be attached to laundry. This makes it easy for the crystals attached to the laundry to be eluted, and thus makes it easy for the treatment substance to exert the effect peculiar thereto in the laundry. Moreover, spraying liquid containing a softening agent in the form of a shower onto laundry, as compared with dipping laundry in liquid containing a softening agent, helps reduce the amount of the softening agent used. Moreover, the smaller the liquid droplets of the shower, the smaller the amount of liquid needed to densely attach the liquid droplets to the surface of laundry.

Still another example of the treatment substance is a sustained-release agent. Also in this case, on the same principle as described above, it is possible to make it easy for the sustained-release agent to exert the effect peculiar thereto.

Here, a sustained-release agent is a material containing silver which, when brought into contact with water, gradually releases the silver ion. Examples include hardly soluble silver sulfide that dissolves gradually, zeolite containing silver that permits the silver ion to be gradually eluted, water-soluble glass containing the silver ion that permits the silver ion to be gradually eluted as the glass dissolves.

In a case where a sustained-release agent is used, it is not possible to control whether or not to effect the releasing (whether or not to effect the elution of silver). Thus, it is preferable to provide a separate water feed route and to use this route only when silver is added. Moreover, in a case where a sustained-release agent is used, it is not possible to control the amount of silver eluted. Thus, it is preferable to use a sustained-release agent in applications where the flow rate of water is roughly constant.

In this respect, it is easy to use a sustained-release agent in a construction where, as in the washer incorporating the water feeding apparatus according to the present invention, a low-flow-rate feed route for a shower is provided separately from the feed route via the main feed valve 50a for main feedwater and the feed route via the sub feed valve 50b for the addition of a softening agent, and that separate feed route is used only when the silver ion is added. This is because a low flow rate contributes to keeping the flow rate stable even in the face of variations in the pressure of tap water.

(8-4. Washer)

This embodiment deals with, as an example, a washer of a vertical type, i.e., of the type in which the rotation axis of a washing tub 30 provided therein as a laundry tub in which laundry is put as a target to be fed with water is vertically aligned. It is, however, also possible to apply the washing tub 30 according to the present invention to any type of washer, including horizontal-drum washers that have, as a laundry tub, a drum of which the rotation axis crosses the vertical direction, and two-tub washers.

INDUSTRIAL APPLICABILITY

The water feeding apparatus according to the present invention can be used in, for example, washers and water spraying apparatus (for example, dish washer-dryers, shower apparatuses, and water sprinkling apparatuses).

The invention claimed is:

1. A water feeding apparatus for feeding water to a target to be fed with water, comprising:
an adder for adding a treatment substance to the water; and
a shower emitter for spraying, in a form of a shower, the water fed thereto via the adder onto the target,
wherein the adder is an ion eluter that elutes an antimicrobial and/or antifungal ion as the treatment substance and that adds the ion to the water passing therethrough,
wherein the ion eluter includes
an electrode from which a metallic ion is eluted and
a casing housing the electrodes and having an outflow port through which the water is fed to the shower emitter,
wherein the outflow port includes a first outflow port that is located in a position lower than a lower end of the electrode and a second outflow port that is located in a position higher than a higher end of the electrode, and
wherein at least part of the casing has a curved surface.

2. The water feeding apparatus of claim 1,
wherein the shower emitter repeatedly sprays the shower onto the target.

3. The water feeding apparatus of claim 1,
wherein the shower emitter is composed of a vibrator that atomizes by vibration the water fed thereto via the adder.

4. A method of feeding water whereby water in a form of a shower is sprayed onto a target to be fed with water by use of the water feeding apparatus of claim 1.

5. A washer comprising:
the water feeding apparatus of claim 1; and
a laundry tub in which laundry is put as the target to be fed with water.

6. The washer of claim 5, further comprising:
controlling means for controlling addition of the antimicrobial and/or antifungal ion to the water by the adder in such a way that either a first water containing the antimicrobial and/or antifungal ion or a second water not containing the antimicrobial and/or antifungal ion is sprayed onto the laundry earlier than is the second water or the first water, respectively.

7. The washer of claim 6,
wherein the controlling means performs control such that the shower emitter sprays the first water during at least one of a rinsing process, a spin-drying process, and a drying process.

8. The washer of claim 7,
wherein the controlling means performs control such that spraying of the first water by the shower emitter is turned on and off repeatedly during a drying process.

9. The washer of claim 6,
wherein the controlling means performs control such that the laundry is moved while the first water is being sprayed.

10. The washer of claim 9,
wherein the controlling means performs control such that the laundry tub is rotated while the first water is being sprayed.

11. The washer of claim 9,
wherein the controlling means performs control such that an agitating member for agitating the laundry is rotated while the first water is being sprayed.

12. The washer of claim 8,
wherein the controlling means performs control such that air is blown onto the laundry while the first water is being sprayed.

13. The washer of claim 8,
wherein the treatment substance is a metallic ion.
14. The washer of claim 13,
wherein the metallic ion is a silver ion, and
wherein an amount of metal that is attached to the laundry sprayed with the first water containing the silver ion is 0.1 mg or more per kilogram of laundry.
15. The washer of claim 13,
wherein the metallic ion is a silver ion, and
wherein an amount of metal that is attached to the laundry sprayed with the first water containing the silver ion is less than 19 mg per kilogram of laundry.
16. The washer of claim 13,
wherein the controlling means controls a drain valve for draining water inside the laundry tub in such a way that draining of water is suspended for a predetermined period of time after the shower emitter finishes spraying the water in the form of a shower.
17. The washer of claim 13,
wherein the controlling means performs control such that the laundry tub is rotated for a predetermined period of time after the shower emitter finishes spraying the water in the form of a shower.
18. The washer of claim 13, further comprising:
an input handler for accepting setting of a washing course; and
an operation controller for controlling operation of the washing course set via the input handler,
wherein the laundry tub is a holeless tub, and
wherein, when a tub cleaning course for cleaning the laundry tub is set as the washing course via the input handler, the operation controller controls operation of the tub cleaning course in such a way that the tub is cleaned with an amount of water sufficient to permit an agitating member for agitating the laundry put in the holeless tub to be immersed in the water.
19. The washer of claim 18,
wherein the operation controller controls the operation of the tub cleaning course in such a way that the tub is cleaned with water containing the metallic ion.
20. The washer of claim 13,
wherein the metallic ion is a silver ion, and
wherein an amount of metal that is attached to the laundry sprayed with the first water containing the metallic ion is 0.9 mg or more per kilogram of laundry.
21. The washer of claim 13,
wherein the metallic ion is a silver ion, and
wherein an amount of metal that is attached to the laundry sprayed with the first water containing the metallic ion is 1 mg or more per kilogram of laundry.
22. The washer of claim 13,
wherein the metallic ion is a silver ion, and
wherein an amount of metal that is attached to the laundry sprayed with the first water containing the metallic ion is 10 mg or less per kilogram of laundry.
23. The washer of claim 13,
wherein the metallic ion is a silver ion, and
wherein an amount of metal that is attached to the laundry sprayed with the first water containing the metallic ion is 0.1 mg or more and less than 19 mg per kilogram of laundry.
24. The water feeding apparatus of claim 1,
wherein the shower emitter includes shower emitters provided so as to correspond respectively to the first and second outflow ports, and
wherein the individual shower emitters are connected to the respective outflow ports via connection pipes with height differences left in between.
25. The water feeding apparatus of claim 24,
wherein, of the individual shower emitters, the shower emitter located in a lower position is located in a position lower than a lower end of the electrode of the ion eluter.
26. The water feeding apparatus of claim 1, wherein the casing is substantially cylindrical, elliptic, spherical or spheroidal in shape.
27. The water feeding apparatus of claim 1, wherein the ion eluter further includes terminals that penetrate the casing and by which a voltage is applied to the electrodes, and
wherein the terminals have a substantially circular cross section.

* * * * *